(12) United States Patent
Hudyma et al.

(10) Patent No.: US 6,620,934 B2
(45) Date of Patent: Sep. 16, 2003

(54) WATER SOLUBLE PRODRUGS OF AZOLE COMPOUNDS

(75) Inventors: Thomas W. Hudyma, Durham, CT (US); Oak K. Kim, Guilford, CT (US); Xiaofan Zheng, Meriden, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 5 days.

(21) Appl. No.: 09/965,755

(22) Filed: Sep. 28, 2001

(65) Prior Publication Data

US 2002/0049216 A1 Apr. 25, 2002

Related U.S. Application Data

(62) Division of application No. 09/441,541, filed on Nov. 16, 1999, now abandoned.
(60) Provisional application No. 60/109,184, filed on Nov. 20, 1998.

(51) Int. Cl.$^7$ ...................... C07D 403/14; C07F 9/6658
(52) U.S. Cl. ........................................ 544/337; 544/366
(58) Field of Search .................. 544/366, 337

(56) References Cited

U.S. PATENT DOCUMENTS

| | | |
|---|---|---|
| 5,648,372 A | 7/1997 | Naito et al. |
| 5,707,977 A | 1/1998 | Heeres et al. |
| 5,714,490 A * | 2/1998 | Saksena et al. ............. 514/252 |
| 5,883,097 A | 3/1999 | Lovey et al. |
| 5,900,486 A * | 5/1999 | Ichihara et al. ............. 544/364 |
| 6,043,245 A * | 3/2000 | Bennett et al. ............. 514/252 |

FOREIGN PATENT DOCUMENTS

| | | |
|---|---|---|
| EP | 829478 A2 | 3/1998 |
| WO | WO 96/38443 | 12/1996 |
| WO | WO 97/28169 | 8/1997 |
| WO | WO 98/34934 | 8/1998 |
| WO | WO 98/43970 | 10/1998 |
| WO | WO 99/15522 | 4/1999 |
| WO | WO 99/33846 | 7/1999 |

OTHER PUBLICATIONS

Law et al., "Activity of SCH 56592 compared with those of fluconazole, etc.," CA 127:328818 (1997).*
Pfaller et al., "Activity of a new triazole, Sch 56592, compared, etc.," CA 126: 197287 (1997).*

* cited by examiner

Primary Examiner—Patricia L. Morris
(74) Attorney, Agent, or Firm—Warren K. Volles

(57) ABSTRACT

Water-soluble prodrugs of triazole antifungal compounds having a secondary or tertiary hydroxy group are provided. More particularly, new water-soluble triazole antifungal compounds are provided having the general formula

I $$(HO)_2(O)PO-[CH_2]_m-\overset{R^1}{\underset{R^2\ R^3}{\text{Ar}}}-R^4-C(O)-[O-]_p-[C(O)-O]_n-A$$

wherein A is the non-hydroxy portion of a triazole antifungal compound of the type containing a secondary or tertiary hydroxyl group and n, m, p, $R^1$, $R^2$, $R^3$, and $R^4$ are as defined in the specification.

1 Claim, No Drawings

WATER SOLUBLE PRODRUGS OF AZOLE COMPOUNDS

CROSS-REFERENCE TO RELATED APPLICATIONS

This divisional application claims the priority of U.S. application Ser. No. 09/441,541 filed Nov. 16, 1999, now abandoned, which claims the benefit of U.S. Provisional Application Serial No. 60/109,184 filed Nov. 20, 1998, abandoned.

BACKGROUND OF THE INVENTION

This invention relates to a new class of azole derivatives, methods for their use, and processes for their production. The compounds described herein are useful for the treatment of fungal infections in humans and other mammals. The present invention provides a compound represented by the general formula:

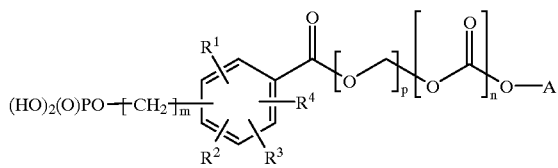

I wherein A is the non-hydroxy portion of a triazole antifungal compound of the type containing a secondary or tertiary hydroxy group, n is 0 or 1, m can be 0 to 6; p is 1 or 2; $R^1$, $R^2$, $R^3$ and $R^4$ can each independently be hydrogen, $C_1$–$C_6$ alkyl, hydroxy, $OR^5$, $NH_2$, $NR^6R^7$, or halogen; $R^5$, $R^6$ and $R^7$ can each independently be hydrogen, C(O)R8, or $C_1$–$C_6$ alkyl; $R^8$ is $C_1$–$C_6$ alkyl, or a pharmaceutically acceptable salt thereof.

DESCRIPTION OF THE PRIOR ART

Triazole antifungal compounds are well known in the prior art. Of the several known classes of such compounds, one particularly potent class contains a tertiary hydroxyl group. For example, U.S. Pat. No. 5,648,372 discloses that (2R,3R)-3-[4-(4-cyanophenyl)thiazol-2-yl]-2-(2,4-difluorophenyl)-1-(1H-1,2,4-triazol-1-yl)-butan-2-ol has potent anti-fungal activity.

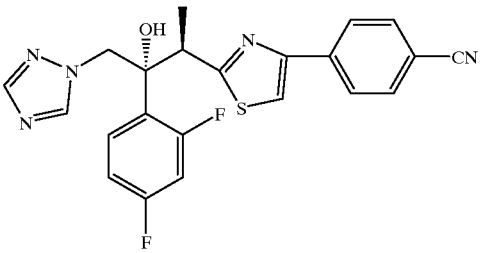

The utility of this class of compounds is limited by their low water solubility. Various prior art methods have attempted to address this problem in order to prepare water-soluble forms of these compounds, e.g. for parenteral administration.

WO 97/28169 discloses compounds of the general formula

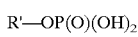

R'—OP(O)(OH)$_2$ wherein R' represents the non-hydroxy portion of a triazole antifungal compound of the type containing a tertiary hydroxy group.

EP 829478 discloses compounds of the general formula

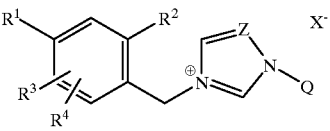

wherein Q is the remainder of an azole compound of the formula

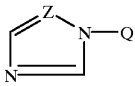

possessing antifungal activity;

Z is nitrogen or methine;

$R^1$ and $R^2$ are each independently a hydrogen atom or a group —OY in which Y is a group easily hydrolyzable under physiological condition;

$R^3$ and $R^4$ are each independently a hydrogen or halogen atom, lower alkyl, lower alkoxy, lower alkylthio, (lower alkylcarbonyl)-thiomethyl, carboxy or methoxycarbonyl; and X is a pharmaceutically acceptable anion.

WO 99/15522 discloses compounds of the general formula

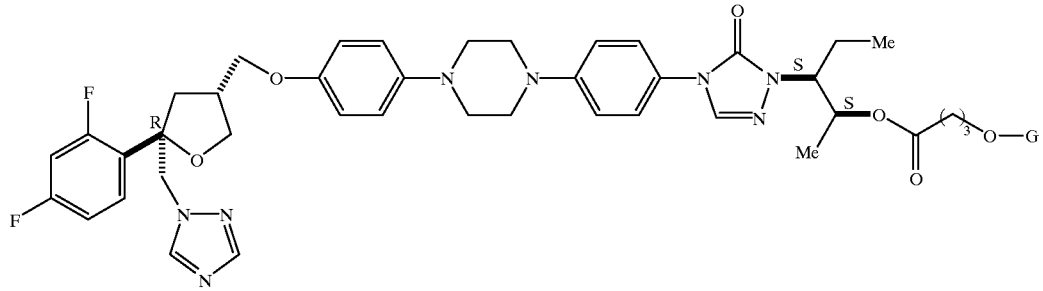

wherein G is H or PO$_3$H$_2$.

WO 98/34934 discloses compounds of the formula

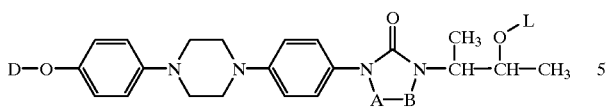

the N-oxide forms, the pharmaceutically acceptable addition salts and stereochemically isomeric forms thereof, wherein —A—B— forms a divalent radical of formula:

—N=CH— (a),

—CH=N— (b),

—CH=CH— (c), wherein one hydrogen atom in the radicals (a) and (b) may be replaced with a $C_{1-6}$ alkyl-radical and up to two hydrogen atoms in radical (c) may be replaced by a $C_{1-6}$ alkyl-radical;

L represents the acyl moiety of an amino acid, and thus —O—L represents an amino acid ester group;

D is a radical of formula

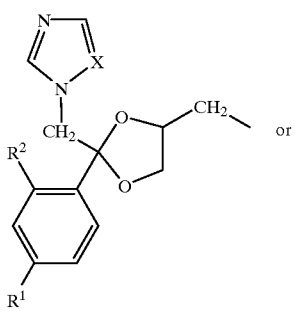 or (D₁)

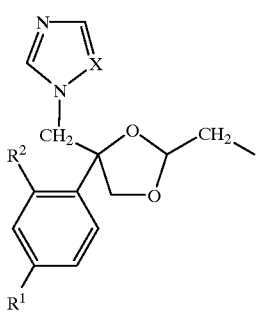

(D₂)

wherein X is N or CH;

$R^1$ is halo;

$R^2$ is hydrogen or halo.

U.S. Pat. No. 5,707,977 discloses compounds of the formula

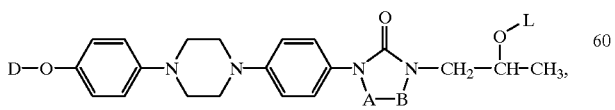

an acid or base addition salt thereof or a stereochemically isomeric form thereof, wherein A and B taken together form —N=CH—, —CH=N—, —CH₂—CH₂—, CH=CH—, —C(=O)—CH₂—, —CH₂—C(=O); D is a radical of formula

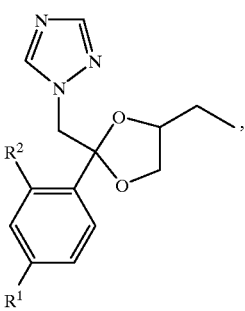

(D₁)

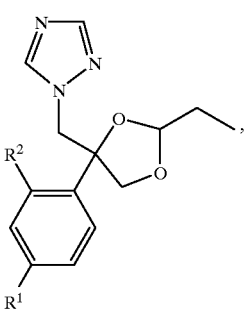

(D₂)

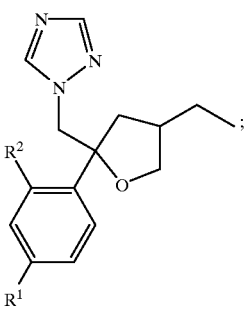

(D₃)

L is a radical of formula

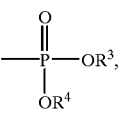

(L₁)

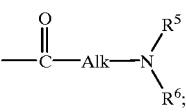

(L₂)

Alk is a $C_{14}$ alkanediyl radical; $R^1$ is halo; $R^2$ is hydrogen or halo; $R^3$ is hydrogen, $C_{1-6}$ alkyl, phenyl or halophenyl; $R^4$ is hydrogen, $C_{1-6}$ alkyl, phenyl or halophenyl; $R^5$ is hydrogen or $C_{1-6}$ alkyl; $R^6$ is hydrogen, $C_{1-6}$ alkyl, $C_{1-6}$ alkyloxycarbonyl, or $R^5$ and $R^6$ taken together with the nitrogen atom to which they are attached form a heterocyclic ring.

WO 96/38443 discloses compounds of the formula

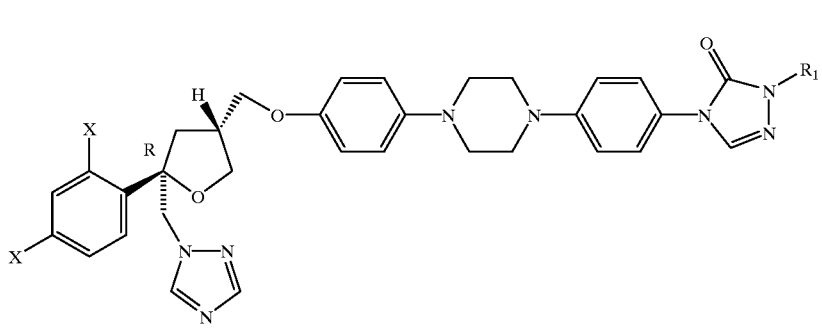

[I]

wherein X is independently both F or both Cl or one X is independently F and the other is independently Cl;

$R_1$ is a straight or branched chain ($C_4$–$C_5$) alkyl group substituted by one or two groups convertible in vivo into hydroxy moieties or a pharmaceutically acceptable salt thereof.

WO 98/43970 discloses a quaternized nitrogen-containing imidazol-1-yl or 1,2,4-triazol-1-yl compound wherein one of the nitrogen atoms constituting an azole ring is quaternized with a substituent capable of being eliminated in vivo to be converted into an antifungal azole compound. The preferred compounds have the formula

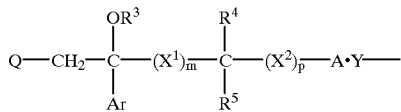

(Ia)

(wherein Q is an imidazol-1-yl or 1,2,4-triazol-1-yl group in which one of the nitrogen atoms constituting an azole ring is quaternized with a substituent capable of being eliminated in vivo; Ar is an optionally substituted phenyl group; A is an optionally substituted hydrocarbon group or an optionally substituted heterocyclic group; $X^1$ is an oxygen atom or a methylene group; $X^2$ is an optionally oxidized sulfur atom; m and p respectively represent 0 or 1; Y is an anion; and (1) $R^3$, $R^4$ and $R^5$ may be the same or different and represent a hydrogen atom or a lower alkyl group, or (2) $R^3$ is a hydrogen atom or a lower alkyl group and $R^4$ and $R^5$ are combined with each other to form a lower alkylene group, or (3) $R^5$ is a hydrogen atom or a lower alkyl group and $R^3$ and $R^4$ are combined with each other to form a lower alkylene group) or a salt thereof.

WO 99/33846 discloses compounds of the formula

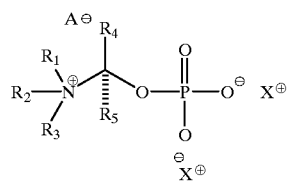

wherein $R_1$, $R_2$ and $R_3$ are substituents which comprise the parent secondary or tertiary amidne such that one of $R_1$, $R_2$ or $R_3$ may be hydrogen, $R_4$ and $R_5$ are each hydrogen, or an organic or inorganic residue.

U.S. Pat. No. 5,883,097 discloses the water-soluble lactic acid addition salt of the compound represented by the formula

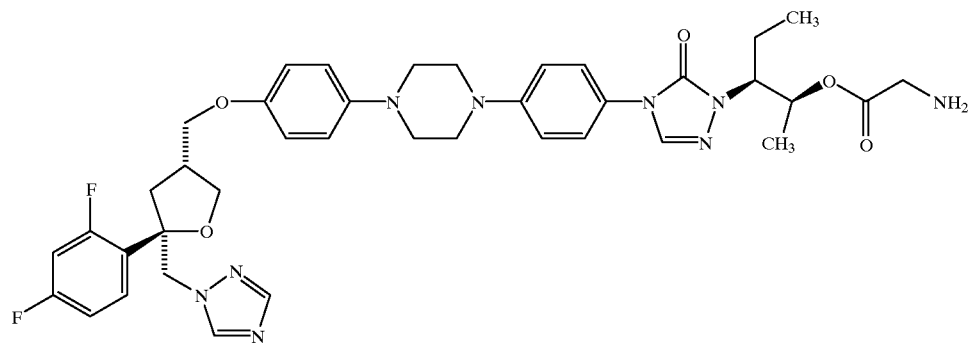

as suitable for preparation of pharmaceutical formulations for intravenous use.

SUMMARY OF THE INVENTION

It has now been found that triazole anti-fungal compounds containing a secondary or tertiary hydroxyl group, including (2R,3R)-3-[4-yl)-butan-2-ol, may be converted into pro-drugs with superior properties to those previously disclosed by attaching a phosphate containing moiety via a linking group. Specifically, the invention covers compounds of the formula:

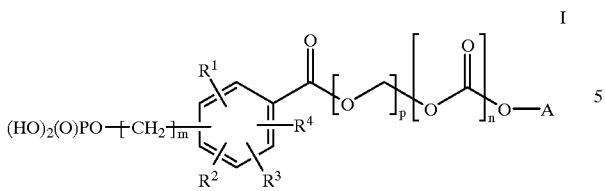

I wherein A is the non-hydroxy portion of a triazole antifungal compound of the type containing a secondary or tertiary hydroxy group, n is 0 or 1, m can be 0 to 6; p is 1 or 2; $R^1$, $R^2$, $R^3$ and $R^4$ can each independently be hydrogen, $C_1$–$C_6$ alkyl, hydroxy, $OR^5$, $NH_2$, $NR^6R^7$, or halogen; $R^5$, $R^6$ and $R^7$ can each independently be hydrogen, C(O)R8, or $C_1$–$C_6$ alkyl; $R^8$ is $C_1$–$C_6$ alkyl, or a pharmaceutically acceptable salt thereof. The preferred formula I compounds are those where $R^1$, $R^2$, $R^3$ and $R^4$ are each independently hydrogen, $C_1$–$C_6$ alkyl, $OR^5$ or halogen. Most preferred are the formula I compunds where $R^1$, $R^2$, $R^3$ and $R^4$ are each hydrogen.

In a preferred embodiment, A represents the non-hydroxy portion of a triazole antifungal compound of the type containing a tertiary hydroxy group.

The various phosphate containing substituents of formula I may be attached in either an ortho, meta, or para relationship to the ester substituent, with the preferred attachment being either meta or para.

In a preferred embodiment A can be

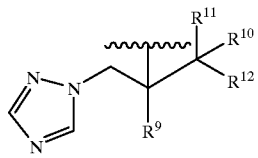

II wherein $R^9$ represents phenyl substituted by one or more (preferably 1–3) halogen atoms;

$R^{10}$ represents H or $CH_3$;

$R^{11}$ represents H, or taken together with $R^{10}$ may represent $=CH_2$;

$R^{12}$ represents a 5- or 6 membered nitrogen containing ring which may be optionally substituted by one or more groups selected from halogen, =O, phenyl substituted by one or more groups selected from CNi, $(C_6H_4)$—$OCH_2CF_2CHF_2$ and CH=CH—$(C_6H_4)$—$OCH_2CF_2CHF_2$, or phenyl substituted by one or more groups selected from halogen and methylpyrazolyl.

Nitrogen containing heterocycles which $R^{12}$ may represent include triazolyl, pyrimidinyl, and thiazolyl.

Preferred embodiments comprise:

(1) A compound of formula I where A is a group of formula II and $R^9$ is 2,4-difluorophenyl; or a pharmaceutically acceptable salt thereof;

(2) A compound of (1) above where $R^{10}$ is methyl and Rll is hydrogen; or a pharmaceutically acceptable salt thereof;

(3) A compound of (2) above where $R^{12}$ is 4-(4-cyanophenyl)-thiazol-2-yl; or a pharmaceutically acceptable salt thereof;

(4) A compound of (3) above wherein n is 0 or 1, m is 0 or 1, p is 1 and $R^1$, $R^2$, $R^3$ and $R^4$ are each hydrogen; or a pharmaceutically acceptable salt thereof.

Specific examples of A include, but are not limited to, the following:

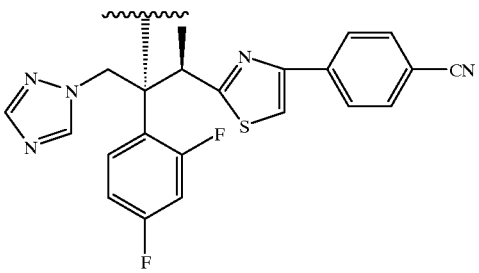

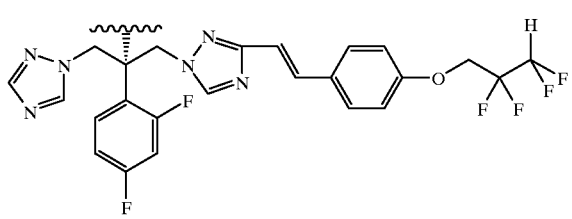

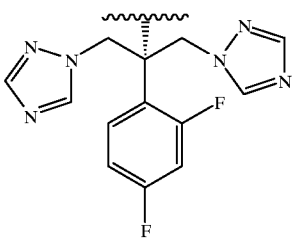

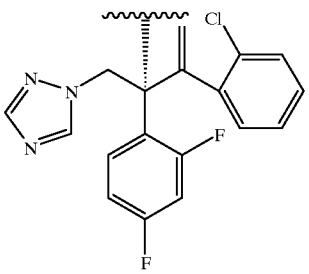

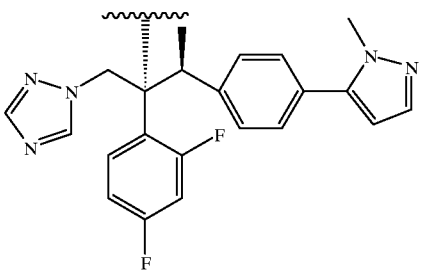

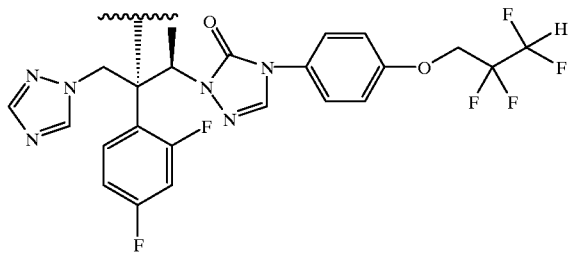

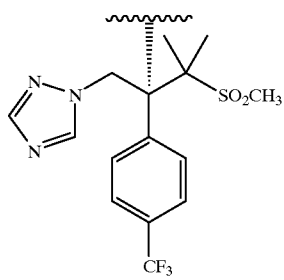 and
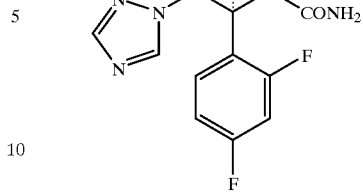
In addition to the application of the present invention to structures containing a tertiary alcohol, it should also be understood that this discovery can be applied to anti-fungal agents which contain secondary alcohols. Some examples include, but are not limited to, the following:
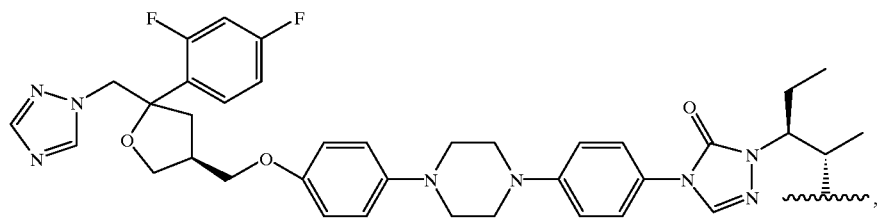
,
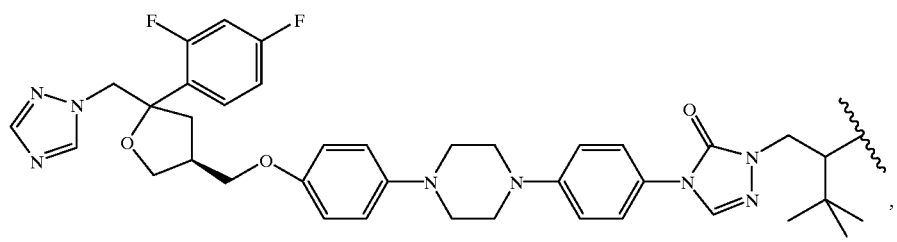
,
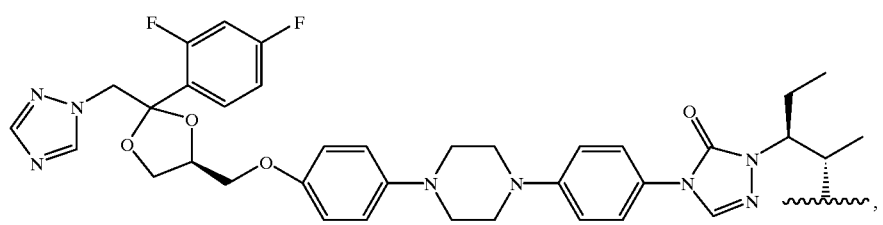
,
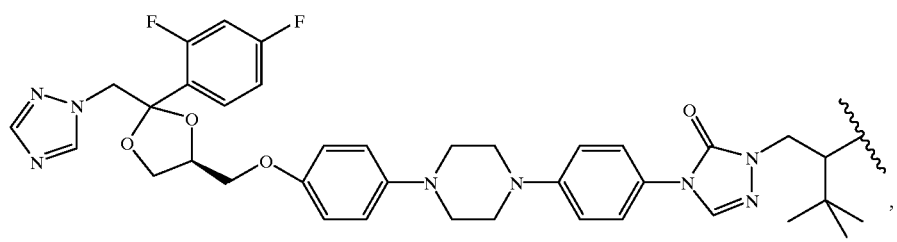
,
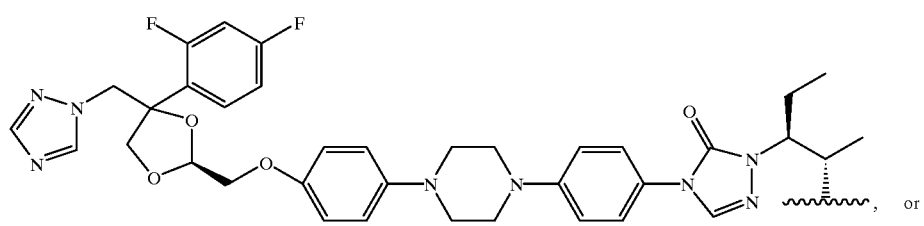
, or

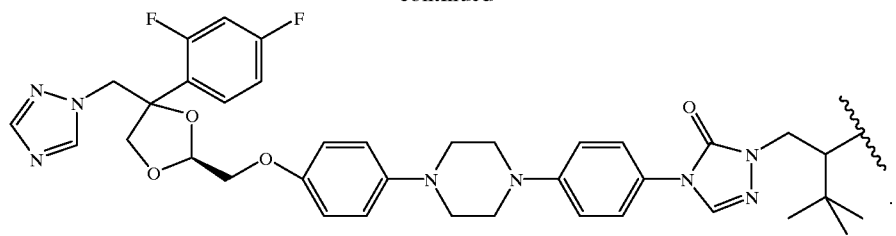
Representative values for m, n, and p are shown below:
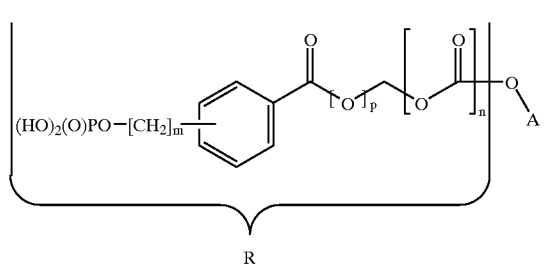
(where A represents the non-hydroxy portion of a triazole anti-fungal compound of the type containing a tertiary or secondary hydroxyl group)
| R |
|---|
| 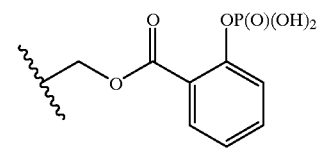 |
| 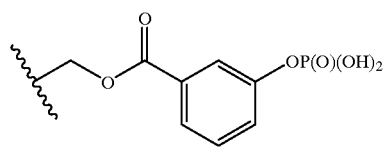 |
| 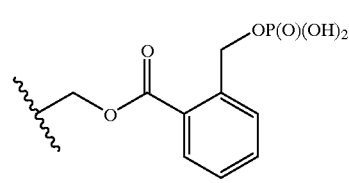 |
| R |
|---|
| 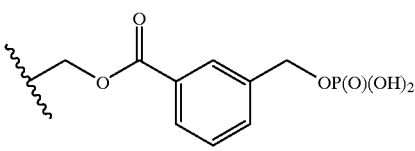 |
| 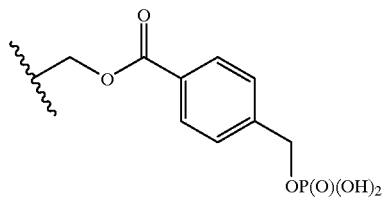 |
| 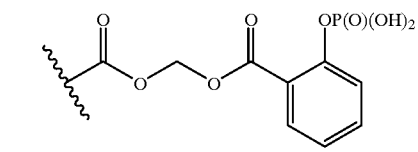 |
| 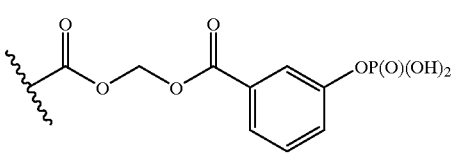 |
| 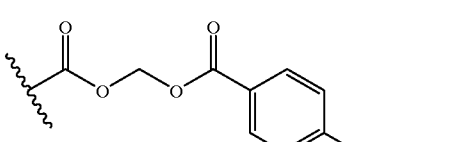 |
| 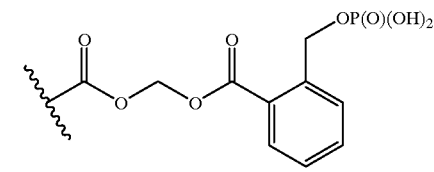 |
| 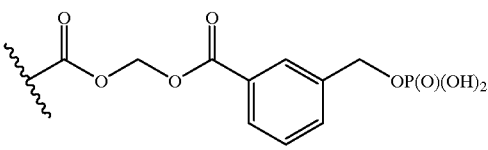 |

| -continued |
| :---: |
| R |
| 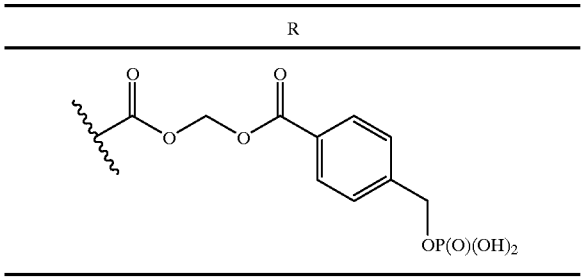 |

DEFINITIONS

The term "pharmaceutically acceptable salt" as used herein is intended to include salts with such counterions as ammonium, alkali metal salts, particularly sodium or potassium, alkaline earth metal salts, particularly calcium or magnesium, and salts with suitable organic bases such as lower alkylamines (methylamine, ethylamine, cyclohexylamine, and the like) or with substituted lower alkylamines (e.g. hydroxyl-substituted alkylamines such as diethanolamine, meglumine (N-methylglucamine), eglumine, triethanolamine or tris(hydroxymethyl) aminomethane). Salts with bases such as piperidine or morpholine are also intended to be encompassed by the term "pharmaceutically acceptable salt".

The term "halogen" includes chloro, bromo, fluoro and iodo, and is preferably chloro or fluoro, and most preferably fluoro.

The aliphatic "alkyl" groups may be straight or branched chains having the specified number of carbon atoms, e.g. in the case of $C_1$–$C_6$ alkyl, the alkyl group may have from 1 to 6 carbon atoms.

DETAILED DESCRIPTION

Preferred embodiments of the present invention, including in each case pharmaceutically acceptable salts thereof are:

(2R,3R)-3-[4-(4-cyanophenyl)thiazol-2-yl]-2-(2,4-difluorophenyl)-1-(1H-1,2,4-triazol-1-yl)-2-[[[o-phosphonooxy]benzoyloxy]-methoxy]butane (compound of example 1)

(2R,3R)-3-[4-(4-cyanophenyl)thiazol-2-yl]-2-(2,4-difluorophenyl)-1-(1H-1,2,4-triazol-1-yl)-2-[[[p-phosphonooxymethyl]benzoyloxy]-methoxy]butane (compound of example 2)

(2R,3R)-3-[4-(4-cyanophenyl)thiazol-2-yl]-2-(2,4-difluorophenyl)-1-(1H-1,2,4-triazol-1-yl)-2-[[[m-phosphonooxymethyl]benzoyloxy]-methoxy]butane (compound of example 3)

(2R,3R)-3-[4-(4-cyanophenyl)thiazol-2-ylj-2-(2,4-difluorophenyl)-1-(1H-1,2,4-triazol-1-yl)-2-[[[p-phosphonooxymethyl]benzoyloxy]-methoxy]carbonyloxy]butane (compound of example 4)

(2R,3R)-3-[4-(4-cyanophenyl)thiazol-2-yl]-2-(2,4-difluorophenyl)-1-(1H-1,2,4-triazol-1-yl)-2-[[[m-phosphonooxy]benzoyloxy]methoxy]butane (compound of example 5)

(2R,3R)-3-[4-(4-cyanophenyl)thiazol-2-yl]-2-(2,4-difluorophenyl)-1-(1H-1,2,4-triazol-1-yl)-2-[[[p-phosphonooxy]benzoyloxy]methoxy]butane (2R,3R)-3-[4-(4-cyanophenyl)thiazol-2-yl]-2-(2,4-difluorophenyl)-1-(1H-1,2,4-triazol-1-yl)-2-[[[o-phosphonooxymethyl]benzoyloxy]methoxy]butane (2R,3R)-3-[4-(4-cyanophenyl)thiazol-2-yl]-2-(2,4-difluorophenyl)-1-(1H-1,2,4-triazol-1-yl)-2-[[[o-phosphonooxymethyl]benzoyloxy]methoxy]carbonyloxy]butane (2R,3R)-3-[4-(4-cyanophenyl)thiazol-2-yl]-2-(2,4-difluorophenyl)-1-(1H-1,2,4-triazol-1-yl)-2-[[[m-phosphonooxymethyl]benzoyloxy]methoxy]carbonyloxy]butane (2R,3R)-3-[4-(4-cyanophenyl)thiazol-2-yl]-2-(2,4-difluorophenyl)-1-(1H-1,2,4-triazol-1-yl)-2-[[[m-phosphonooxy]benzoyloxy]methoxy]carbonyloxy]butane (compound of example 6)

(2R,3R)-3-[4-(4-cyanophenyl)thiazol-2-yl]-2-(2,4-difluorophenyl)-1-(1H-1,2,4-triazol-1-yl)-2-[[[p-phosphonooxy]benzoyloxy]methoxy]carbonyloxy]butane (compound of example 6)

(2R,3R)-3-[4-(4-cyanophenyl)thiazol-2-yl]-2-(2,4-difluorophenyl)-1-(1H-1,2,4-triazol-1-yl)-2-[[[o-phosphonooxy]benzoyloxy]methoxy]carbonyloxy]butane (compound of example 6)

The aforementioned preferred embodiments of the present invention are listed in the table below.

III

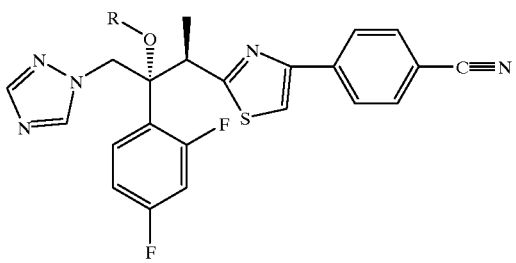

| Example | R |
| :---: | :---: |
| 1 | 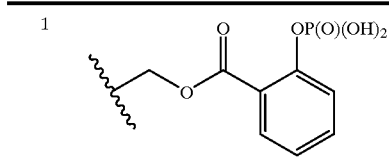 |
| 2 | 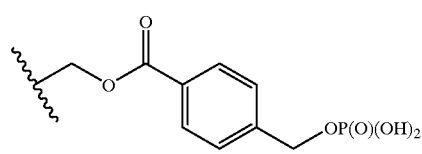 |
| 3 | 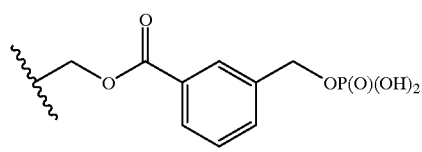 |

III
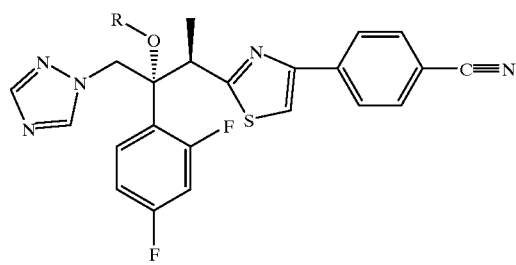
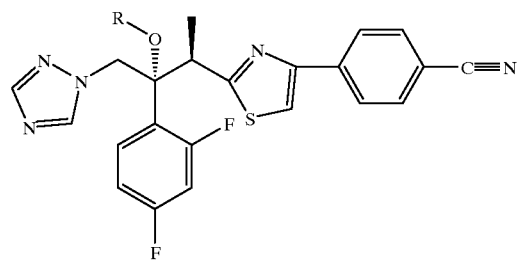
| Example | R |
|---|---|
| 4 | 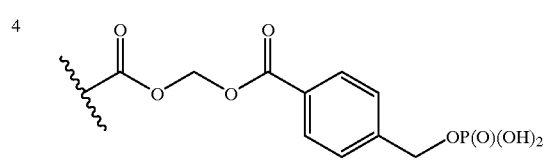 |
| 5 | 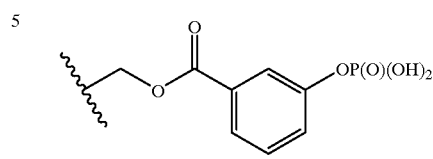 |
| 6 | 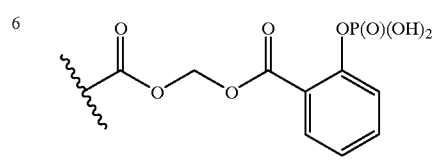 |
| Example | R |
|---|---|
|  | 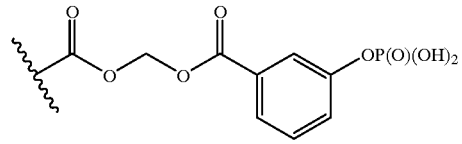 |
|  | 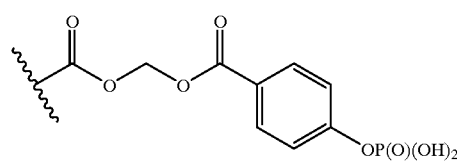 |
The compounds of the present invention can be made by conventional methods. Three suitable general procedures are summarized by the following reaction schemes. In these schemes, A represents the non-hydroxy portion of a triazole anti-fungal compound of the type containing a secondary or tertiary hydroxyl group.
Method 1
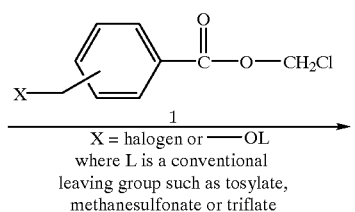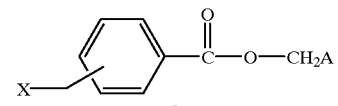
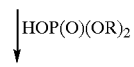
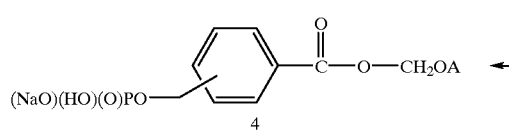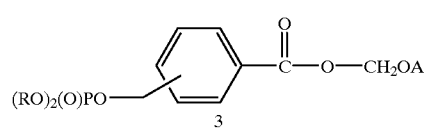

Method 2
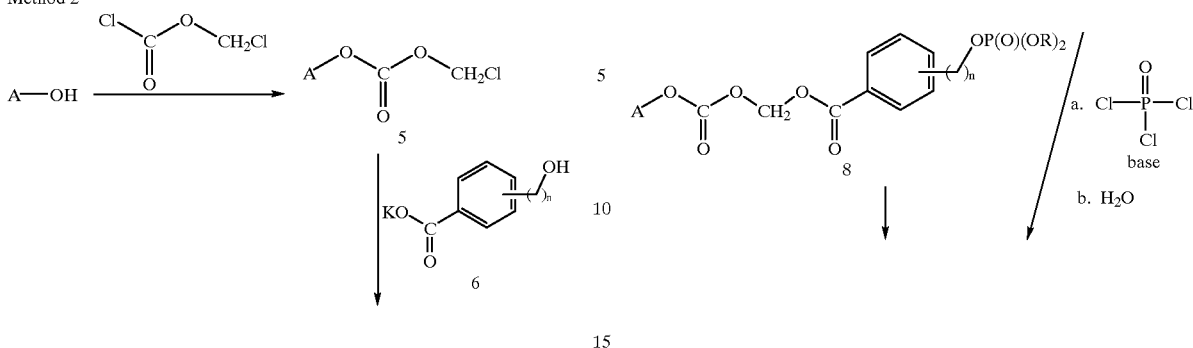
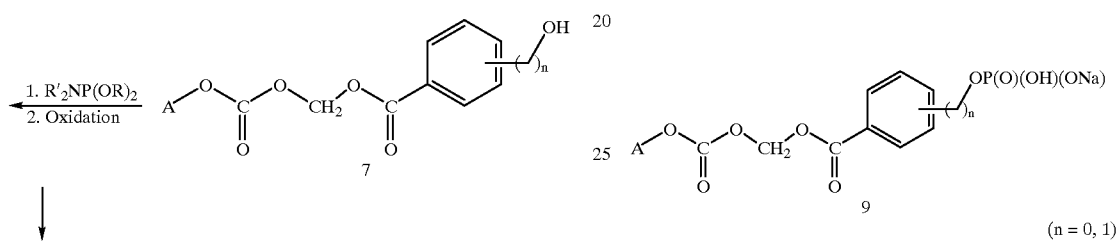
Method 3
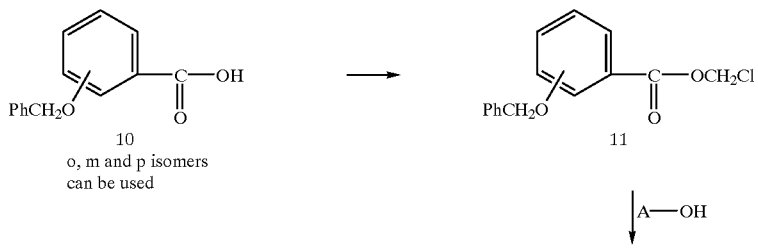
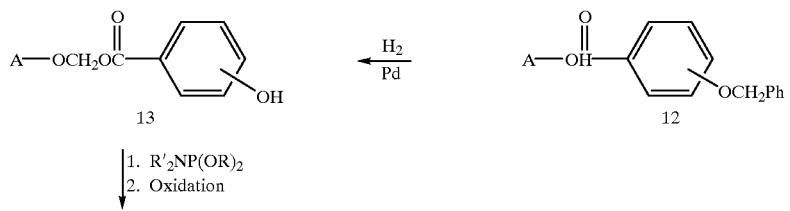
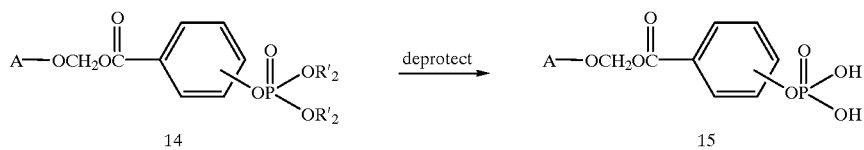

To elaborate on Method 1, the anti-fungal parent compound of interest is converted into ester 2 by reaction with chloride intermediate 1 in the presence of a suitable base, such as potassium hydride. The esterification reaction can be carried out in THF (tetrahydrofuran) or other inert organic solvent and the product may be purified by column chromatography. Chloride 1 can be prepared by the method of Iyer et al. found in *Syn. Comm.* 25, 2739, (1995) (see "Preparation of Starting Materials" herein, Method 1) or by the alternative method disclosed below in "Preparation of Starting Materials," Method 2. Ester 2 can be subsequently converted into phosphate ester 3 by reaction with a dialkyl phosphate in refluxing acetonitrile. Phosphate ester 3 can be converted to the phosphate acid 4 in one of two ways. If phosphate 4 is the di-tertiary butyl ester, the free phosphate acid can be liberated by treatment with trifluoroacteic acid. Alternatively, if phosphate 4 is the di-benzyl ester, the free phosphate acid can be obtained by hydrogenation in the presence of palladium on carbon in the presence of a suitable solvent. In either case, the final product can be purified via C-18 column chromatography.

To elaborate on Method 2, the anti-fungal parent compound of interest is converted into chloromethylformate 5 by reaction with commercially available chloromethyl chloroformate in the presence of an appropriate base in THF or other solvent at 0° C. to 50° C. Appropriate bases include potassium hydride and sodium hydride, among others, with the preferred base being potassium hydride. The product 5 may be purified by column chromatography. Chloromethylformate 5 is converted to alcohol 7 by reaction with carboxylate salt 6 in acetonitrile or other appropriate organic solvent. Carboxylate salt 6 can be prepared by the method disclosed in U.S. Pat. No. 4,623,486. Alcohol 7 can be converted to phosphate ester 8 by reaction with a commercially available phosphoramidite in the presence of tetrazole followed by oxidation e.g. by use of hydrogen peroxide or m-chloroperoxybenzoic acid. Ester 8 can be purified by column chromatography. Phosphate ester 8 can then be converted to phosphate acid 9 in one of two ways. If phosphate 8 is the di-tertiary butyl ester, the free phosphate acid can be liberated by treatment with trifluoroacteic acid. Alternatively, if phosphate 8 is the di-benzyl ester, the free phosphate acid can be obtained by hydrogenation in the presence of palladium on carbon in the presence of a suitable solvent. Alternatively, phosphate acid 9 can be prepared from alcohol 7 by reaction with phosphorus oxychloride in an inert organic solvent such as dichloromethane in the presence of an organic base such as pyridine. In either case, the final product can be purified via C-18 column chromatography.

To elaborate on Method 3 the benzyloxybenzoic acids 10 are converted to their respective chloromethyl esters 11 using the procedures described for the preparation of compounds 1 in Method 1. The anti-fungal parent compound of interest is then converted to either its potassium or sodium salt by reaction with either potassium or sodium hydride respectively, in an inert solvent such as THF (tetrahydrofuran), or DMF (N,N-dimethylformamide), or mixtures of both at 0° C. to 60° C. The chloromethyl esters 11 are then introduced to the reaction mixtures to afford the intermediates 12. The compounds 12 can be purified by column chromatography on silicic acid. The benzyl protecting groups are removed from the compounds 12 by hydrogenation using palladium catalysts in an inert solvent to give the alcohols 13 which can be purified by flash chromatography on silicic acid. The alcohols 13 are coverted to the phosphate esters by reaction with a commercially available phosphoramidite in the presence of tetrazole followed by oxidation e.g. by the use of hydrogen peroxide or m-chloroperoxybenzoic acid. The phosphate esters 14 are converted to their respective phosphate acids 15 by one of the two methods illustrated in Method 2 for the conversion of 8 to 9.

In another aspect then, the present invention provides intermediates of the formula

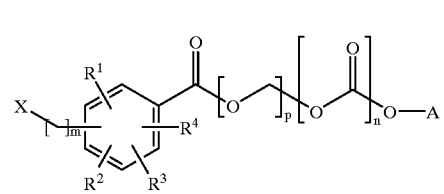

wherein A is the non-hydroxy portion of a triazole antifungal compound of the type containing a secondary or tertiary hydroxy group; n is 0 or 1; m is 0 to 6; p is 1 or 2; $R^1$, $R^2$, $R^3$ and $R^4$ can each independently be hydrogen, $C_{1-6}$ alkyl, hydroxy, $OR^5$, $NH_2$, $NR^6R^7$ or halogen; and X is OH or —OL where L is a conventional leaving group such as tosylate, methanesulfonate or triflate; and pharmaceutically acceptable salts thereof.

A preferred embodiment comprises the intermediates of formula III wherein A represents the non-hydroxy portion of a triazole antifungal compound of the type containing a tertiary hydroxy group. Within this preferred embodiment, A is preferably a group of the formula II above. A most preferred embodiment within this subclass comprises compounds where $R^9$ in formula II is 2,4-difluorophenyl. Another most preferred embodiment comprises compounds where $R^9$ is 2,4-difluorophenyl, $R^{10}$ is methyl and $R^{11}$ is hydrogen. A still more preferred embodiment of this subclass comprises compounds wherein $R^9$ is 2,4-difluorophenyl, $R^{10}$ is methyl, $R^{11}$ is hydrogen and $R^{12}$ is 4-(4-cyanophenyl)thiazol-2-yl.

A preferred embodiment comprises intermediates of formula III wherein n is 0, p is 1, $R^1$, $R^2$, $R^3$ and $R^4$ are hydrogen, m is 0 or 1, and X is OH.

Another preferred embodiment comprises intermediates of formula III wherein n is 1, p is 1, $R^1$, $R^2$, $R^3$ and $R^4$ are hydrogen, m is 0 or 1 and X is OH.

Another preferred aspect of the present invention comprises the intermediates of the formula

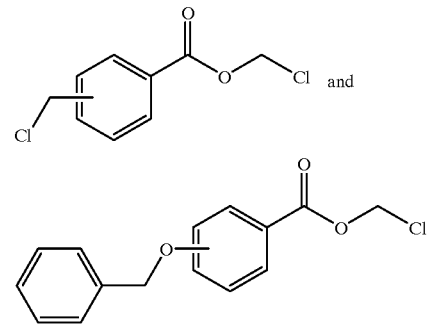

It will be understood that where the substituent groups used in the above reactions contain certain reaction sensitive functional groups such as amino or carboxylate groups which might result in undesirable side-reactions, such groups may be protected by conventional protecting groups known to those skilled in the art. Suitable protecting groups and methods for their removal are illustrated, for example, in *Protective Groups in Organic Synthesis,* Theodora W. Greene (John Wiley & Sons, 1991). It is intended that such "protected" intermediates and end-products are included within the scope of the present disclosure and claims.

The desired end-product of formula I may be recovered in the form of a pharmaceutically acceptable acid salt. As defined previously, the term "pharmaceutically acceptable salt" as used herein is intended to include salts with such counterions as ammonium, alkali metal salts, particularly sodium or potassium, alkaline earth metal salts, particularly calcium or magnesium, and salts with suitable organic bases such as lower alkylamines (methylamine, ethylamine, cyclohexylamine, and the like) or with substituted lower alkylamines (e.g. hydroxyl-substituted alkylamines such as diethanolamine, triethanolamine or tris(hydroxymethyl) aminomethane), or with bases such as piperidine or morpholine, and meglumine and eglumine.

It will be appreciated that certain products within the scope of formula I may have substituent groups which can result in formation of optical isomers. It is intended that the present invention include within its scope all such optical isomers as well as epimeric mixtures thereof, i.e. R- or S- or racemic forms.

The pharmaceutically active compounds of this invention may be used alone or formulated as pharmaceutical compositions comprising, in addition to the active triazole ingredient, a pharmaceutically acceptable carrier, adjuvant or diluent. The compounds may be administered by a variety of means, for example, orally, topically or parenterally (intravenous or intramuscular injection). The pharmaceutical compositions may be in solid form such as capsules, tablets, powders, etc. or in liquid form such as solutions, suspensions or emulsions. Compositions for injection may be prepared in unit dose form in ampules or in multidose containers and may contain additives such as suspending, stabilizing and dispersing agents. The compositions may be in ready-to-use form or in powder form for reconstitution at the time of delivery with a suitable vehicle such as sterile water.

Alternatively, the compounds of the present invention can be administered in the form of a suppository or pessary, or they may be applied topically in the form of a lotion, solution, or cream. Additionally, they may be incorporated (at a concentration up to 10%) into an ointment consisting of a white wax or soft, white paraffin base together with the required stabilizers and/or preservatives.

The compounds of the invention are useful because they possess pharmacological activities in animals, including particularly mammals and most particularly, humans. Specifically, the compounds of the present invention are useful for the treatment or prevention of topical fungal infections, including those caused by species of Candida, Trichophyton, Microsporum, or Epidermophyton. Additionally, they are useful for the treatment of mucosal infections caused by *Candida albicans.* They can also be used in the treatment of systemic fungal infections caused, for example, by species of *Candida albicans, Cryptococcus neoformans, Aspergillus flavus, Aspergillus fumigatus,* Coccidioides, Paracoccidiodes, Histoplasma, or Blastomyces.

Thus, according to another aspect of the invention, there is provided a method of treating a fungal infection which comprises administering a therapeutically effective amount of the compound to a host, particularly a mammalian host and most particularly a human patient. The use of the compounds of the present invention as pharmaceuticals and the use of the compounds of the invention in the manufacture of a medicament for the treatment of fungal infections are also provided.

The dosage to be administered depends, to a large extent, on the particular compound being used, the particular composition formulated, the route of administration, the nature and condition of the host and the particular situs and organism being treated. Selection of the particular preferred dosage and route of application, then, is left to the discretion of the physician or veterinarian. In general, however, the compounds may be administered parenterally or orally to mammalian hosts in an amount of from about 5 mg/day to about 1.0 g/day. These doses are exemplary of the average case, and there can be individual instances where higher or lower dosages are merited, and such dosages are within the scope of this invention. Furthermore, administration of the compounds of the present inventions can be conducted in either single or divided doses.

The in vitro evaluation of the antifungal activities of the compounds of the invention can be performed by determining the minimum inhibitory concentration (MIC). The MIC is the concentration of test compound which inhibits the growth of the test microorganism. In practice, a series of agar plates, each having the test compound incorporated at a specific concentration, is inoculated with a fungal strain and each plate is then incubated for 48 h at 37° C. The plates are examined for the presence or absence of fungal growth, and the relevant concentration is noted. Microorganisms which can be used in the test include *Candida albicans, Asperigillus fumigatus,* Trichophyton spp., Microsporum spp., *Epidermophyton floccosum, Coccidioides immitis,* and *Torulopsos galbrata.* It should be recognized that, as prodrugs, some compounds of the invention may not be active in the in vitro test.

The in vivo evaluation of compounds of the present invention can be carried out at a series of dose levels by intraperitoneal or intravenous injection or by oral administration to mice which have been inoculated with a strain of fungus (e.g. *Candida albicans*). Activity is determined by comparing the survival of the treated group of mice at different dosage levels after the death of an untreated group of mice. The dose level at which the test compound provides 50% protection against the lethal effect of the infection is noted.

The compounds of the present invention substantially increase the solubility of the parent triazole antifungal compound and also release the bioactive parent compound (i.e. function as a prodrug) in human liver S9 experiments.

ILLUSTRATIVE EXAMPLES

The following examples illustrate the invention, but are not intended as a limitation thereof. The abbreviations used in the examples are conventional abbreviations well-known to those skilled in the art. Some of the abbreviations used are as follows:

| | |
|---|---|
| h = | hour(s) |
| rt = | room temperature |
| mol = | mole(s) |
| mmol = | mmole(s) |
| g = | gram(s) |
| THF = | tetrahydrofuran |
| L = | liter(s) |
| mL = | milliliter(s) |

-continued

| | |
|---|---|
| Et₂O = | diethyl ether |
| EtOAc = | ethyl acetate |
| MeOH = | methanol |
| DMF = | dimethylformamide |
| DABCO = | 1,4-Diazabicyclo[2.2.2]octane |
| TFA = | trifluoroacetic acid |
| DMAP = | dimethylaminopyridine |
| MCPBA = | m-chloroperoxybenzoic acid |
| Ph = | phenyl |
| CH$_3$CN = | acetonitrile |
| EtOH = | ethanol |
| Bn = | benzyl |
| KH = | potassium hydride |
| $^t$Bu = | tertiary butyl |

In the following examples, all temperatures are given in degrees Centigrade. Melting points were determined on an electrothermal apparatus and are not corrected. Proton nuclear magnetic resonance ($^1$H NMR) spectra were recorded on a Bruker AM-300 or a Varian Gemini 300 spectrometer. All spectra were determined in CDCl$_3$, DMSO-d$_6$, CD$_3$OD, or D$_2$O unless otherwise indicated. Chemical shifts are reported in δ units relative to tetramethylsilane (TMS) or a reference solvent peak and interproton coupling constants are reported in Hertz (Hz). Splitting patterns are designated as follows: s, singlet; d, doublet; t, triplet; q, quartet; m, multiplet; br, broad peak; dd, doublet of doublets; dt, doublet of triplets; and app d, apparent doublet, etc. Mass spectra were recorded on a Kratos MS-50 or a Finnegan 4500 instrument utilizing direct chemical ionization (DCI, isobutene), fast atom bombardment (FAB), or electron ion spray (ESI).

Analytical thin-layer chromatography (TLC) was carried out on precoated silica gel plates (60F-254) and visualized using UV light, iodine vapors, and/or staining by heating with methanolic phosphomolybdic acid. Column chromatography, also referred to as flash chromatography, was performed in a glass column using finely divided silica gel at pressures somewhat above atmospheric pressure.

The preparative HPLC purifications were carried out using a Shimadzu LC-8A preparative liquid chromatograph with a 20×100 mm YMCS5 ODS column. The compounds were eluted with CH$_3$OH and water with 0.1% of TFA.

Preparation of Starting Materials

Preparation of (3-Chloromethyl)Benzoic Acid Chloromethyl Ester

A.

Method 1

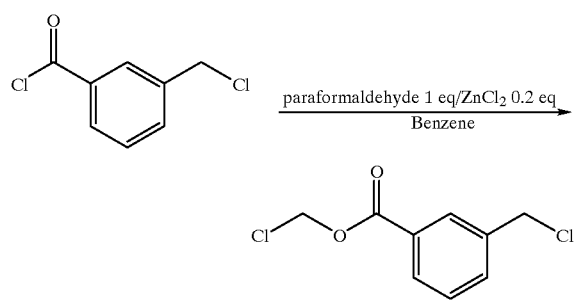

To a cooled (0° C.) mixture of paraformaldehyde (0.79 g, 26.4 mmol) and zinc chloride (72 mg, 0.53 mmol) in benzene (10 mL) was added dropwise the acid chloride (5.0 g, 26.4 mmol) over a period of 15 minutes. The mixture was then heated at 55° C. overnight. The mixture was then filtered and the filtrate concentrated. Purification of the crude product via flash chromatography (100% Hexanes) yielded 2.7 g of the title compound as a colorless oil.

B.

Method 2

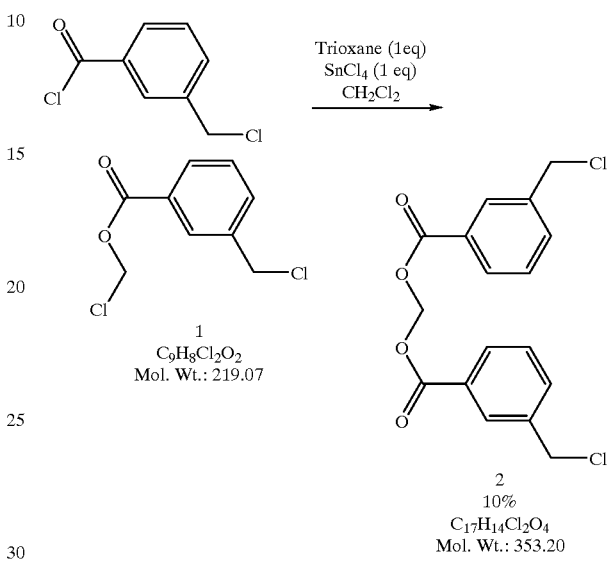

MATERIALS

3-Chloromethylbenzoyl chloride: 30 g (0.159 mole, 22.6 mL, Aldrich)
Tin (IV) Chloride: (41.35 g, 18.57 mL, 158 mole, Aldrich)
1,3,5-trioxane (14.29 g of 99% purity, 0.158 mole, Aldrich)
Dichloromethane (120 mL, EM Science, HPLC grade, KF=0.2 mG/mL)
Heptane (470 mL, EM Science, HPLC grade)
Ethylacetate (4.5 mL, EM Science, HPLC grade)
Aq. NaHCO$_3$ solution (saturated); 100 ml
Water (Deionised, 220 mL)

PROCEDURE

A 500 ml three neck round bottom flash equipped with a nitrogen inlet, reflux condenser, addition funnel, mechanical stirrer and immersion thermometer was charged with 60 mL CH$_2$Cl$_2$ (KF=0.2 mg/mL) and 3-chloromethylbenzoylchloride. Tin (IV) chloride was added via the addition funnel with stirring over a period of 2 minutes maintaining a temperature of 20° C.–22° C. 1,3,5-trioxane was added to the stirred mixture. The majority of the 1,3,5-trioxane remains undissolved.

The stirred suspension was kept at 20° C.–22° C. for 24 hours at the end of which the conversion was 99% (L.C. area percent). Approximately 10% of the dimer (2) was also observed by HPLC.

The reaction mixture was quenched by the addition of 120 mL water via the addition funnel maintaining the internal temperature between 15° C.–20° C.

The reaction mixture (containing some suspended solid particles) was filtered through a sintered glass funnel (polish filtration) and the solids were washed with 120 mL CH$_2$Cl$_2$. After settling, the two layers clearly separated.

The lower CH$_2$Cl$_2$ layer containing the product was separated from the top aqueous layer. The organic layer was washed with 100 mL water and the lower CH$_2$Cl$_2$ layer containing the product was separated from the top aqueous layer.

The lower CH₂Cl₂ layer containing the product was separated from the top aqueous layer. The organic layer was washed with 100 mL saturated aq. NaHCO₃ solution and the lower CH₂Cl₂ layer containing the product was separated from the top aqueous layer.

The lower CH₂Cl₂ layer containing the product was separated from the top aqueous layer. The CH₂Cl₂ was then replaced by heptane via distillation (under atmospheric pressure) maintaining a total volume of approximately 450 mL.

1. Distillation was discontinued when the batch temperature reached approximately 80° C. NMR analysis of the mixture indicated complete removal of CH₂Cl₂ at this point.

2. Approximately 470 mL heptane was used.

The mixture was cooled down to 22° C. Ethylacetate (4.5 mL) was added to the stirred mixture and the stirred mixture was kept at 22° C. for 18 h.

1. The less soluble methanediol bis [3-chloromethyl) benzoate] (2) is crystallized out in this process. Addition of ethylacetate helps to keep the desired product (1) in solution.

2. When the heptane solution is cooled down to approximately 30–40° C., some crystallization of the dimer was observed and a seed bed is formed.

3. If the dimer does not crystallize by cooling down to 22° C., additional cooling to 0–5° C. may be necessary for the seed bed to be formed.

The crystals (dimer 2) were filtered and washed with 60 mL heptane.

1. Approximately 4.4 gm of the dimer, methanediol bis [3-chloromethyl)benzoate] was obtained.

The combined filtrate and wash containing the product was concentrated via distillation under house vacuum to approximately 100 mL volume. The mixture was cooled to 22° C. over a period of one hour with seeding (at 35° C.).

1. Crystallization begins at approximately 30° C. to 35° C.
2. Since the compound melts at 42° C., the mixture should not be seeded above 40° C.

The stirred mixture was cooled to 0–5° C. over a period of 30 minutes and then kept at 0–5° C. for 2 hours. The crystals were filtered, washed with 20 mL of cold (10° C.) heptane, and dried in a vacuum oven at 20–22° C. with a flow of nitrogen for 18 hours to yield 25.8 g (74% yield).

ANALYSES:
M.P. = 41–42° C.
NMR = consistent with the structure.
HPLC

| Instrument: | Shimadzu LC-10AS |
|---|---|
| HPLC Detector: | Shimadzu SPD M10A Diode Array (260 nm) |
| Column: | YMC ODS AQ 4.6 × 150 mm, S-3 μm, 120A |
| Injection vol: | 10 μL |

Flow Rate: 1.5 mL/min
Run Time: 25 min
Eluent A: CH₃CN/ water 10:90
Eluent B: CH₃CN/water 90:10

-continued

| Gradient Table: | Time (minutes) % | Eluent A | % Eluent B |
|---|---|---|---|
| | 0 | 60 | 40 |
| (linear gradient) | 5 | 60 | 40 |
| | 15 | 0 | 100 |
| | 20 | 0 | 100 |
| | 23 | 60 | 40 |
| | 25 | stop | |

Retention Times:
3-Chloromethylbenzoyl chloride 12.28 min.
3-Chloromethylbenzoic acid (formed by hydrolysis of the acid chloride) 3.46 min.
(3-Chloromethyl)benzoic acid chloromethyl ester 11.67 min.
Methanediol bis [3-chloromethyl)benzoatel (2) 14.67 min.

Preparation of Chloromethyl 3-Benzyloxybenzoate

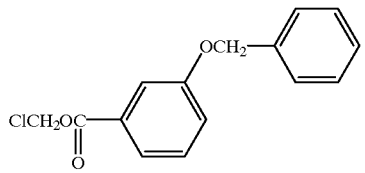

To the potassium salt of 3-benzyloxybenzoic acid (2.39 g, 8.91 mmol) was added the bromochloromethane (8.7 ml, 15 eq.) and DMF (10.7 mL). The mixture was then stirred at room temperature for 12–18 hours. The mixture was then filtered and the filtrate concentrated. Purification of the crude product via flash chromatography (EtOAc: Hexanes 1:10) yielded 1.2 g of the title compound as a light yellow oil. ¹H NMR (300 MHz, CDCl₃) δ=5.12 (s, 2H), 5.96 (s, 2H), 7.22–7.25 (m, 1H), 7.26–7.47 (m, 6H), 7.68–7.72 (m, 2H), MS(ESI) 276.

Example 1

(2R,3R)-3-[4-(4-cyanophenyl)thiazol-2-yl]-2-(2,4-difluorophenyl)-1-(1H-1,2,4-triazol-yl)-2-[[[o-phosphonooxy]benzoyoxy]methoxy]butane

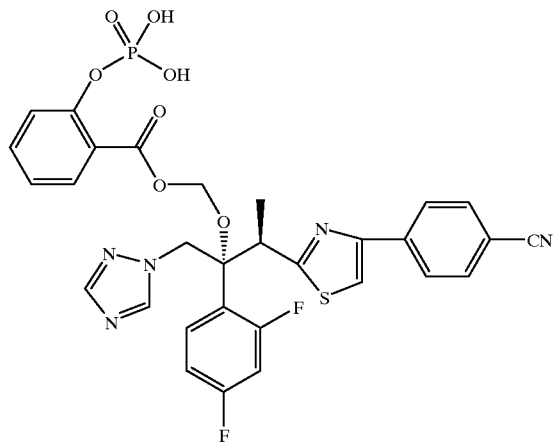

(2R, 3R)-3-L4-(4-cyanophenyl)thiazol-2-yl]-2-(2,4-difluorophenyl)-1-(1H-1,2,4-triazol-1-yl)-2-[[(o-(benzyloxy)benzoyloxy]methoxy]butane

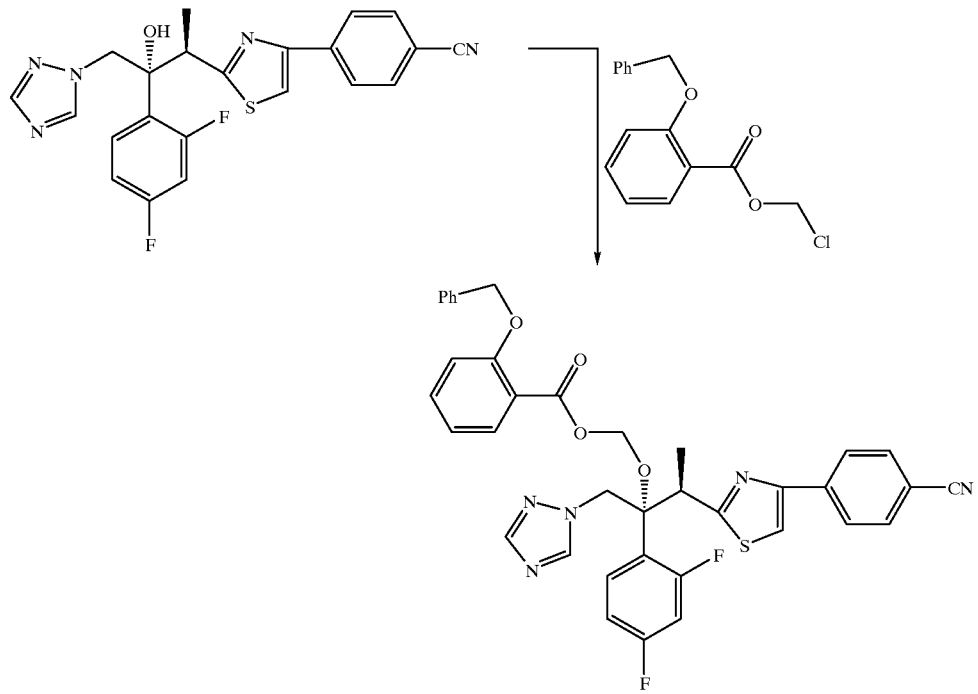

(2R,3R)3-[4-(4-cyanophenyl)thiazol-2-yl]-2-(2,4-difluorophenyl)-1-(1H-1,2,4-triazol-1-yl)butan-2-ol (1.0 mmol) was added to a suspension of potassium hydride (1.1 mmol) in THF (20 mL) at 0° C. The heterogeneous mixture was stirred for 15 minutes and chloromethyl ester (1.1 mmol) was added. The reaction was allowed to stir at r.t. for 5 h. Excess base was carefully quenched with water, and the crude mixture was extracted into ethyl acetate. The organic layer was washed with water, brine and dried over sodium sulfate. Purification of the crude product via flash chromatography (Hexanes/EtOAc) yielded 200 mg of the subtitled compound as a colorless oil. $^1$H NMR (300 MHz, CDCl$_3$) δ=1.27 (d, 3H), 4.06 (q, 1H), 4.87–5.04 (in, 4H), 5.99 (d, 1H), 6.23 (d, 1H), 6.80 (mn, 2H), 6.95 (m, 2H), 7.24–7.45 (m, 8H), 7.66–7.77 (m, 4H), 7.95 (d, 2H), 8.15 (s, 1H). MS (ESI) 677.

(2R,3R)-3-[4-(4-cyanophenyl)thiazol-2-yl]-2-(2,4-difluorophenyl)-1-(1H-1,2,4-triazol-1-yl)-2-[[(o-hydroxy)benzoyloxy]methoxy]butane

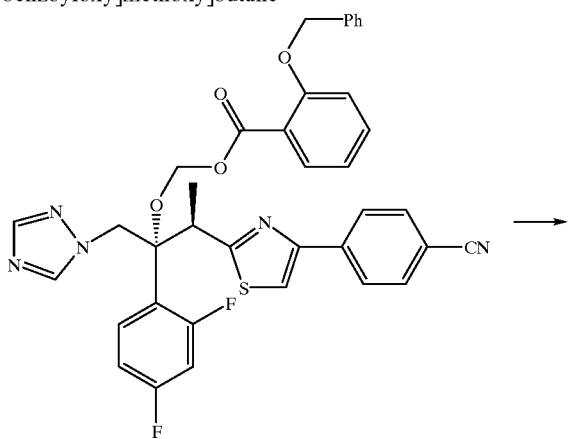

-continued

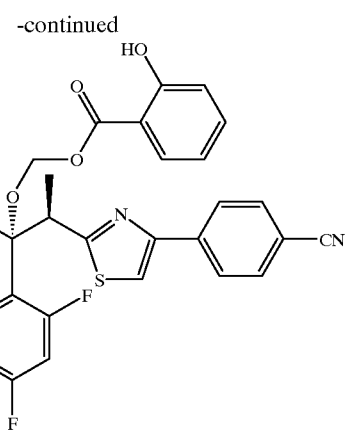

A suspension of (2R,3R)-3-[4-(4-cyanophenyl)thiazol-2-yl]-2-(2,4-difluorophenyl)-1-(1H-1,2,4-triazol-1-yl)-2-[[(o-(benzyloxy)benzoyloxy]methoxy]butane (0.22 mmol) in ethanol (100 mL) was hydrogenated over 10% Palladium on carbon (150 mg) at r.t. at 1 atmosphere for 2.5 h. The crude reaction was concentrated and the filtrate was collected. Purification of the crude product via flash chromatography (Hexanes/EtOAc 3/1) yielded 120 mg of the subtitled compound as a colorless oil. $^1$H NMR (300 MHz, CDCl$_3$) δ=1.27 (d, 3H), 4.12 (m, 1H), 5.02 (d, 1H), 5.28–5.38 (m, 2H), 6.21(dd, 2H), 6.61 (t, 1H), 6.77–6.94 (m, 3H), 7.42 (m, 4H), 7.65 (m, 3H), 7.88 (d, 2H), 8.08 (s, 1H). MS (ESI) 587.

(2R,3R)-3-[4-(4-cyanophenyl)thiazol-2-yl]-2-(2,4-difluorophenyl)-1-(1H-1,2,4-triazol-1-yl)-2-[[[o-dibenzylphosphonooxy]benzoyloxy]methoxy]butane (2R,3R)-3-[4-(4-cyanophenyl)thiazol-2-yl]-2-(2,4-difluorophenyl)-1-(1H-1,2,4-triazol-1-yl)-2-[[[o-phosphonooxy]benzoyloxy]methoxy]butane

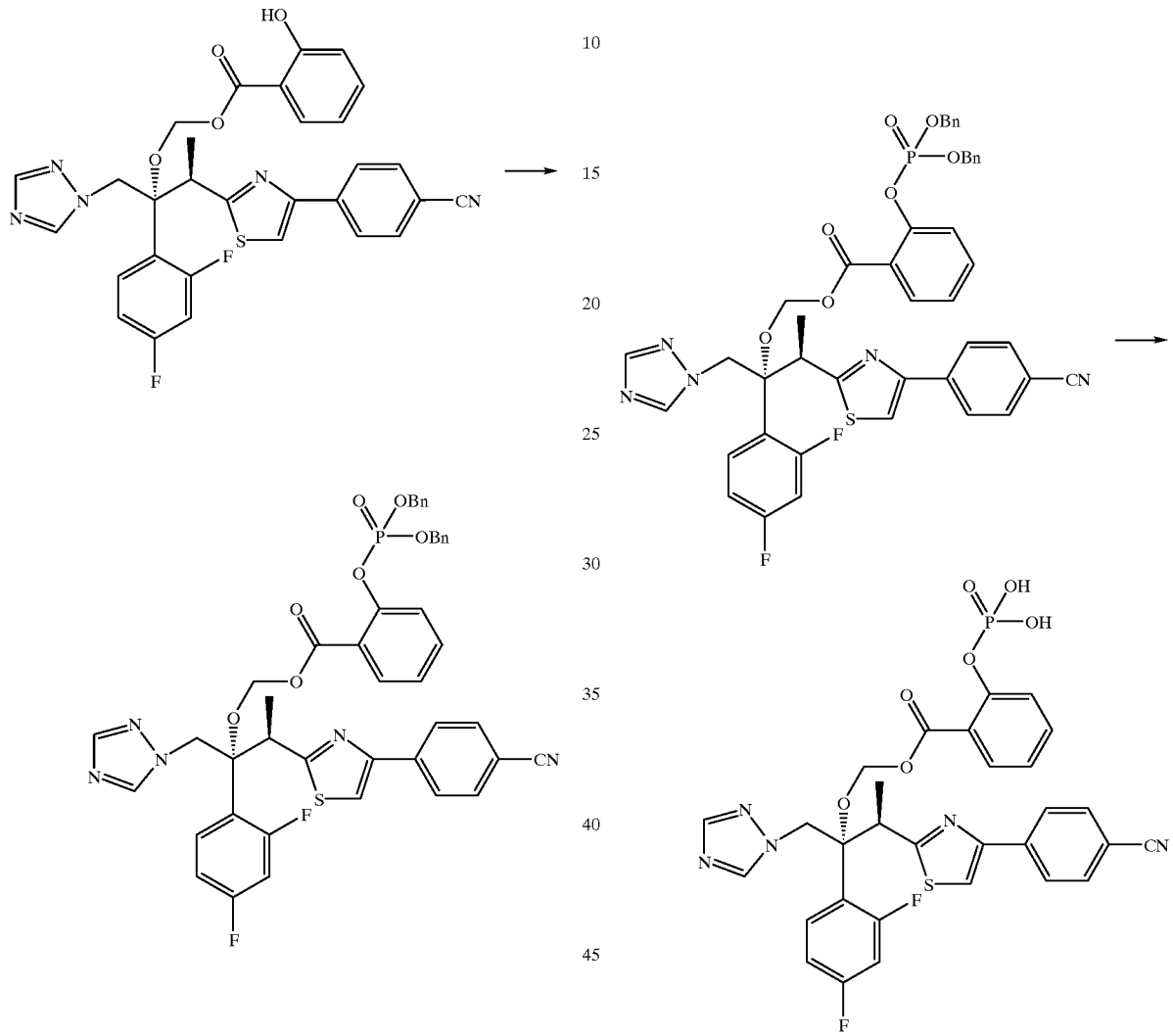

(2R,3R)-3-[4-(4-cyanophenyl)thiazol-2-yl]-2-(2,4-difluorophenyl)-1-(1H-1,2,4-triazol-1-yl)-2-[[[o-hydroxy]benzoyloxy]methoxy]butane (0.22 mmol), 1 H-tetrazole (0.66 mmol), 4-dimethylaminopyridine (10.7 mg, 0.088 mmol) and dibenzyl diisopropylphosphoramidite (0.44 mmol) in methylene chloride (10 mL) were refluxed under a nitrogen atmosphere for 12 h. The mixture was then cooled to 0° C., and hydrogen peroxide (0.25 mL, 30% solution in water) was added dropwise at a rate which maintained the reaction temperature below 20° C. The resulting mixture was stirred at 20° C. for 30 minutes before separating the organic layer, which was washed with water, dried over $Na_2SO_4$. Purification of the crude product via flash chromatography (Hexanes/EtOAc) yielded 140 mg of the subtitled compound as a colorless oil. $^1$H NMR (300 MHz, CDCl$_3$) d=1.28 (d, 3H), 4.10 (q, 1H), 4.96 (d,1H), 5.13–5.21 (m, 4H), 5.27 (d, 1H), 6.07 (d, 1H), 6.14 (d, 1H), 6.76–6.85 (m, 2H), 7.04 (t, 1H), 7.29–7.44 (m, 14H), 7.62–7.67 (m, 4H), 7.90 (d, 2H), 8.10 (s, 1H). MS (ESI) 847

A suspension of (2R,3R)-3-[4-(4-cyanophenyl)thiazol-2-yl]-2-(2,4-difluorophenyl)-1-(1H-1,2,4-triazol-1-yl)-2-[[[o-dibenzylphosphonooxy]benzoyloxy]methoxy]butane (0.17 mmol) in ethanol (100 mL) was hydrogenated over 10% Palladium on carbon (140 mg) at room temperature at 1 atmosphere for one hour. The crude reaction was filtered and the filtrate was collected. Purification of the crude product via flash chromatography (MeOH/CH$_2$Cl$_2$) yielded 80 mg of the titled compound as a white solid. $^1$H NMR (300 MHz, DMSO) d=1.14 (d, 3H), 4.07 (q, 1H), 4.36 (d, 1H), 4.58 (br. s, 2H), 4.85 (d, 2H), 6.94 (t, 1H), 7.08–7.32 (m, 4H), 7.63 (t, 2H), 7.86–7.93(m, 3H), 8.20 (t, 3H), 8.41(s, 1H). MS (ESI) 667.

Example 2
(2R,3R)-3-[4-(4-cyanophenyl)thiazol-2-yl]-2-(2,4-difluorophenyl)-1-(1H-1,2,4-triazol-1-yl)-2-[[[p-phosphonooxymethyl]benzoyloxy]methoxy]butane

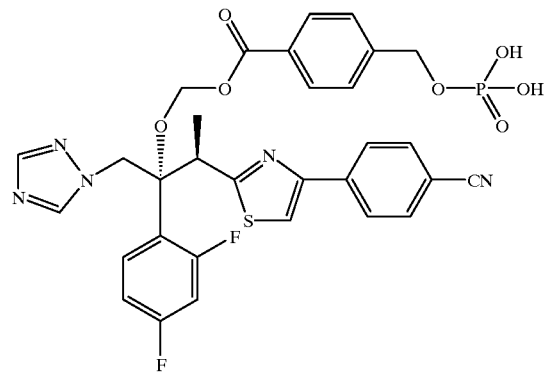

(2R,3R)-3-[4-(4-cyanophenyl)thiazol-2-yl]-2-(2,4-difluorophenyl)-1-(1H-1,2,4-triazol-1-yl)-2-[[[p-dibenzylphosphonooxymethyl]benzoyloxy]methoxy]butane

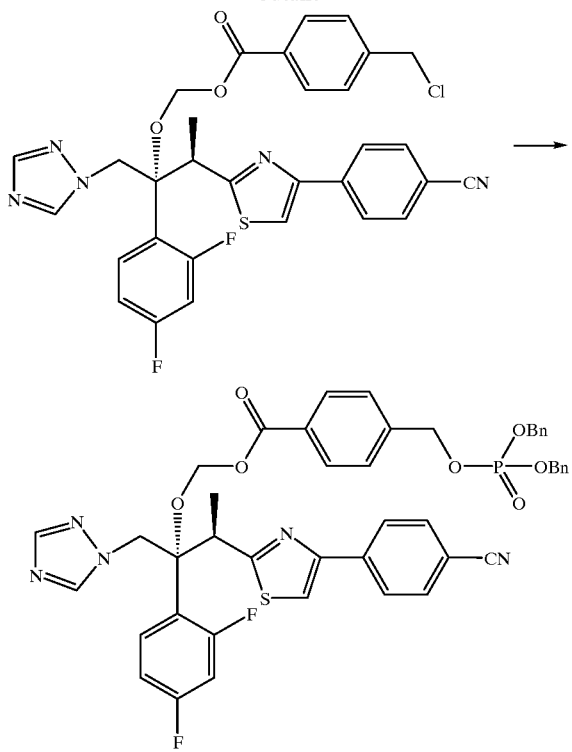

The benzyl chloride (made in by the method disclosed in example C) (300 mg, 0.48 rnmol), di-benzyl phosphate (270 mg, 0.97 mmol), and silver oxide (115 mg, 0.48 mmnol) were disolved in acetonitrile and the rection was allowed to reflux for 7 h. The mixture was cooled, filtered, and the filtrate was diluted with ethyl acetate. This solution was washed with water (2x) and brine, dried over $Na_2SO_4$. Purification of the crude product via flash chromatography (Hexanes/EtOAc) yielded 100 mg of the subtitled compound as a white solid. $^1$H NMR (CDCl$_3$) d 1.31 (d, 3H), 4.13 (q, 1H), 4.97–5.09 (m, 7H), 5.33 (d, 1H), 6.18 (ab, 2H), 6.78 (m, 2H), 7.22–7.46 (m, 17H), 7.68–7.70 (m, 2H), 7.80 (d, 2H), 7.92 (d, 2H), 8.15 (s, 1H). MS: 861.

(2R,3R)-3-[4-(4-cyanophenyl)thiazol-2-yl]-2-(2,4-difluorophenyl)-1-(1H-1,2,4-triazol-1-yl)-2-[[[p-phosphonooxymethyl]benzoyloxy]methoxy]butane

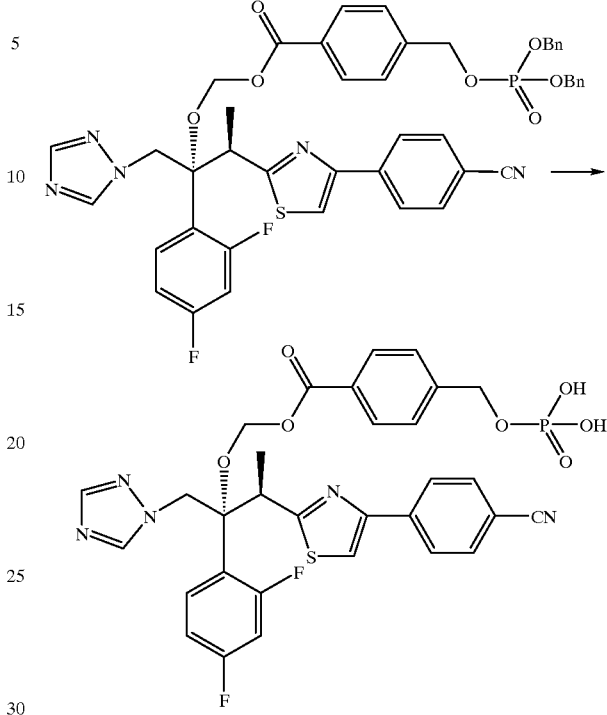

A suspension (2R,3R)-3-[4-(4-cyanophenyl)thiazol-2-yl]-2-(2,4-difluorophenyl)-1-(1H-1,2,4-triazol-1-yl)-2-[[[p-dibenzylphosphonooxymethyl]benzoyloxy]methoxy]butane (0.12 mmol) in EtOAc (100 mL) was hydrogenated over 10% Palladium on carbon (100 mg) at r.t. and 1 atmosphere for 24 h. The crude reaction was filtered and the filtrate was concentrated. Purification of the crude product via prepation HPLC yielded 20 mg of the subtitled compound as a white solid. $^1$H NMR (DMSO) d 1.24 (br. s, 3H), 4.05 (q, 1H), 4.79 (d, 2H), 5.15 (d, 1H), 5.34 (d, 1H), 6.02 (ab, 2H), 7.01 (m, 1H), 7.22 (m, 1H), 7.29(m, 1H), 7.41(d, 2H), 7.77 (d, 2H), 7.84 (s, 1H), 7.88 (d, 2H), 8.06 (d, 2H), 8.20 (s, 1H), 8.51(s, 1H). MS: 681.

Example 3
(2R,3R)-3-[4-(4-cyanophenyl)thiazol-2-yl]-2-(2,4-difluorophenyl)-1-(1H-1,2,4-triazol-1-yl)-2-[[[m-phosphonooxymethyl]]benzoyloxy]methoxy]butane

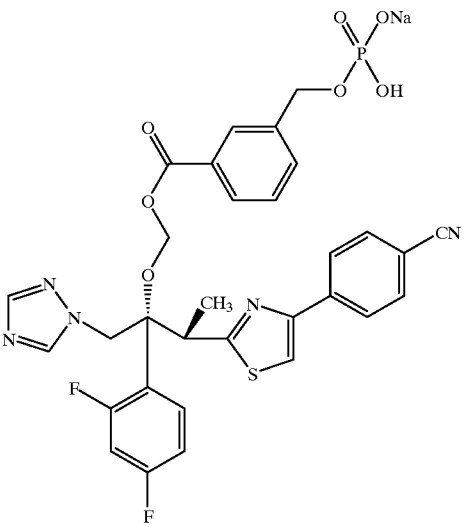

(2R,3R)-3-[4-(4cyanophenyl)thiazol-2-yl]-2-(2,4-difluorophenlyl)-1-(1H-1,2,4-triazol-1-yl)-2-[[[m-chloromethyl]benzoyloxy]methoxy]butane

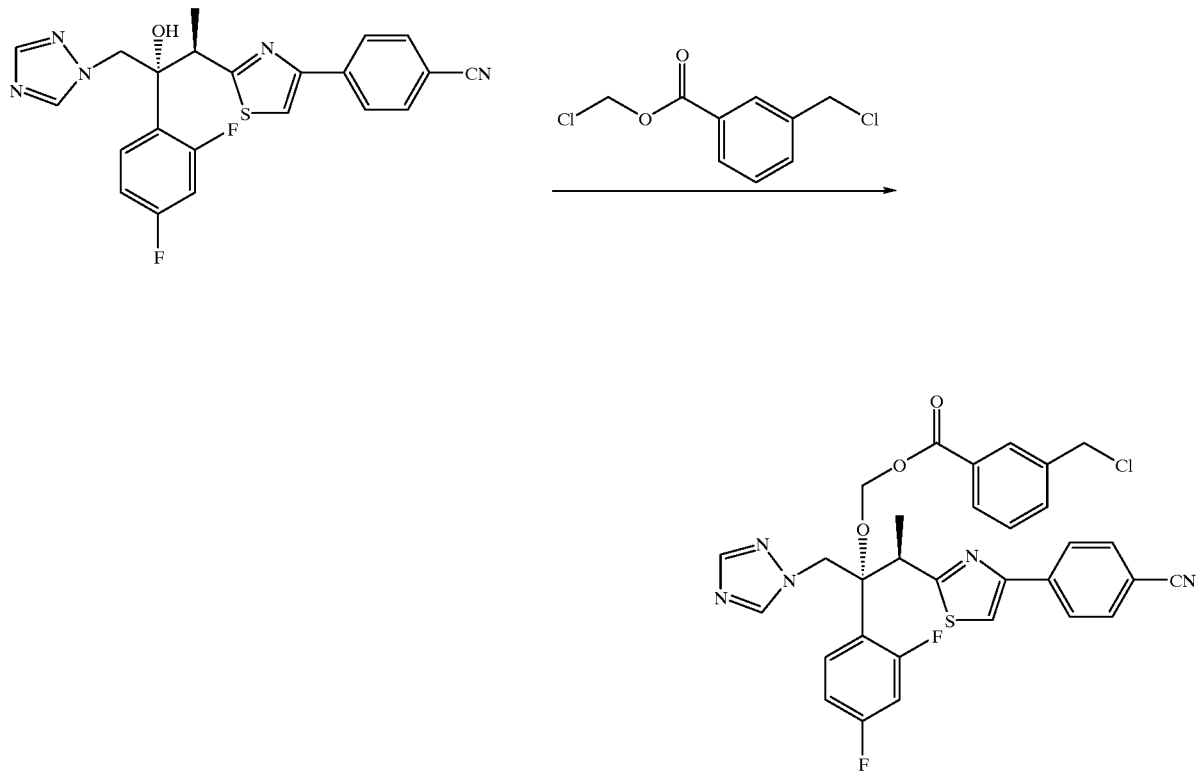

2R,3R)-3-[4-(4-cyanophenyl)thiazol-2-yl]-2-(2,4-difluorophenyl)-1-(1H-1,2,4-triazol-1-yl)butan-2-ol (13.9 mmol) was added to a suspension of potassium hydride (15.3 mmol) in THF (100 mL) at 0° C. The heterogeneous mixture was stirred for 15 minutes and the chloromethyl ester (16.8 mmol, prepared by the method disclosed in Houben-Weyl, Methoden Der Organischen Chemie, Band E14a/3, 85, 1992) was added. The reaction was allowed to stir at 0° C for 2 h and then warmed to r.t. and stirred for 2 h. Excess base was carefully quenched with water, and the crude reaction was extracted into ethyl acetate. The organic layer was washed with water, brine and dried over $Na_2SO_4$. Purification of the crude product via flash chromatography (Hexanes/EtOAc) yielded 4.6 g of the subtitled compound as a colorless oil. $^1$H NMR (CDCl$_3$): δ 1.29 (m, 3H), 4.14 (m, 1H), 5.03 (d, J=16.0, 2H), 5.35 (d, J=18.0, 2H), 6.20 (s, 2H), 6.85 (m, 2H), 7.29(m, 1H), 7.42(m, 2H), 7.56(d, J=7.7, 1H), 7.70(m, 3H), 7.79(d, J=7.8, 1H), 7.88(s, 1H), 7.94(d, J=8.5, 2H), 8.11(s, 1H).

(2R,3R)-3-[4-(4-cyanophenyl)thiazol-2-yl]-2-(2,4-difluorophenyl)-1-(1H-1,2,4-triazol-1-yl)-2-[[[m-di-t-butylphosphonooxymethyl]]benzoyloxy]methoxy]butane

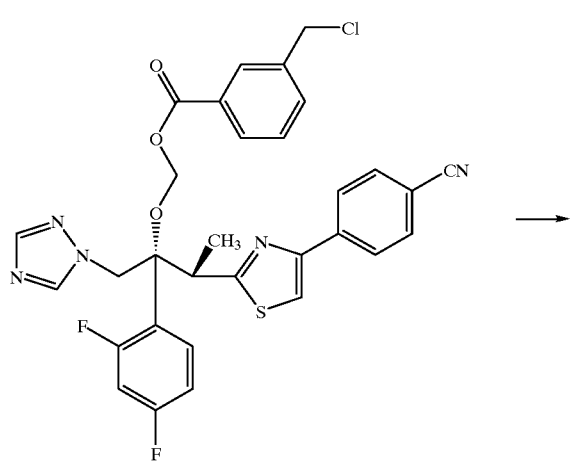

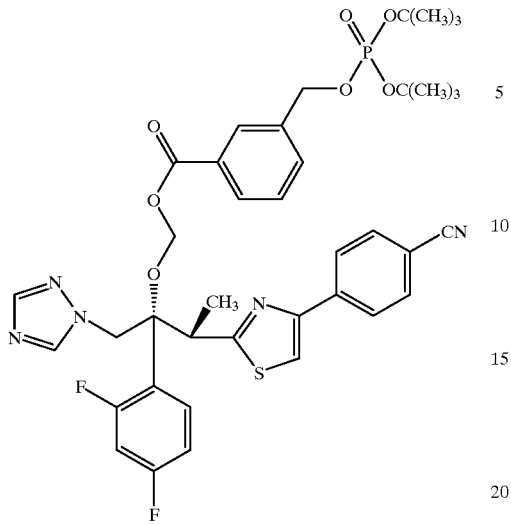

Acetonitrile (160 mL) was added to a mixture of (2R,3R)-3-[4-(4-cyanophenyl)thiazol-2-yl]-2-(2,4-difluorophenyl)-1-(1H-1,2,4-triazol-1-yl)-2-[[[m-chloromethyl]benzoyloxy]methoxy]butane (0.0161mol), di-tert-butyl phosphate (0.0352mol), and silver oxide (0.0177mol). The mixture was stirred under argon and refluxed for 6 hours. The mixture was cooled, filtered, and filtrate was concentrated. The resulting viscous material was dissolved in ethyl acetate. The solution was sequentially washed (dilute sodium bicarbonate followed by saturated brine), dried (magnesium sulfate) and concentrated to afford 12.5 g of the subtitled compound as a viscous oil which was of sufficient purity to carry forward.

(2R,3R)-3-[4-(4-cyanophenyl)thiazol-2-yl]-2-(2,4-difluorophenyl)-1-(1H-1,2,4-triazol-1 yl)-2-[[[m-phosphonooxymethyl]]benzoyloxy]methoxy]butane, sodium salt

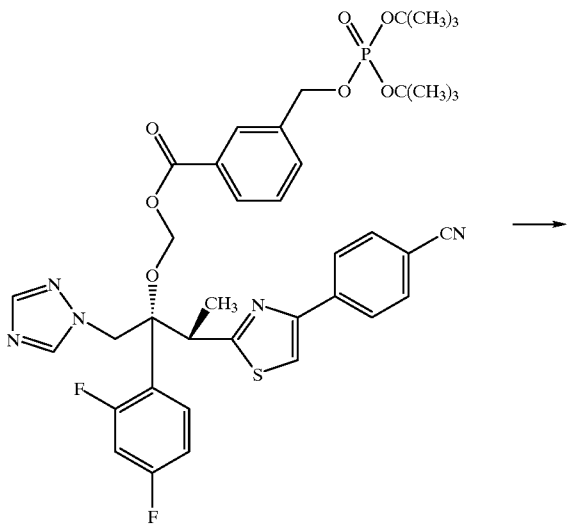

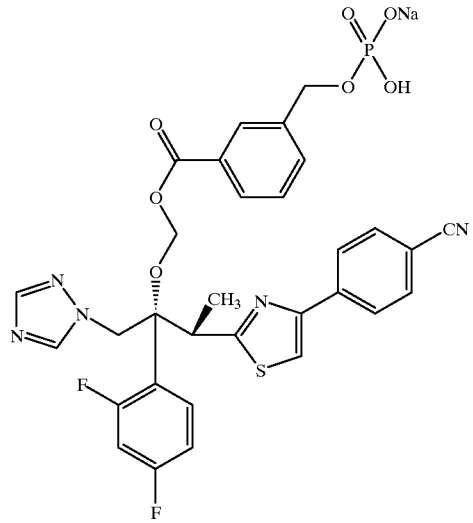

(2R,3R)-3-[4-(4-cyanophenyl)thiazol-2-yl]-2-(2,4-difluorophenyl)-1-(1H-1,2,4-triazol-1-yl)-2-[[[m-di-t-butylphosphonooxymethyl]benzoyloxy]methoxy]butane (11 g) was dissolved in methylene chloride (120 mL). TFA (30 mL) was added and the solution stirred for 15 min. The solution was concentrated to leave a gum. Ice cold saturated sodium bicarbonate (60 mL) was added and the gum worked to give a soft solid. Additional saturated sodium bicarbonate (about 30 mL) was added to give a pH of 6.6 and a largely granular solid. The crude material (2.4g) was dissolved in hot water (about 60° C., 30–40 mL). The hazy solution was filtered (0.45 μm membrane) and applied to a Michel-Miller column (21×250 mm) packed with C18. The column was eluted with water and then with water-acetonitrile (60:40) to elute the product containing fractions. The acetonitrile was removed, and the aqueous solution lyophilized to leave the purified monosodium salt of the title compound (1.53 g) as a colorless solid. $^1$H NMR (CD$_3$OD) δ 1.35 (d, J=7, 3H), 4.19 (q, J=7, 14, 1H), 4.93 (m, 2H), 5.22 (d, J=16, 1H), 5.48 (d, J=16, 1H), 6.19 (m, 2H), 6.97 (m, 2H), 7.28 (m, 1H), 7.49 (m, 1H), 7.68 (m, 2H), 7.71 (m, 3H), 7.91 (s, 1H), 7.96 (s, 1H), 8.00 (m, 2H), 8.00 (m, 2H), and 8.50 (s, 1H); IR (cm-1) 2226 (CN) and 1724 (CO); MH+=682; Anal. Calcd for C$_{31}$H$_{26}$F$_2$N$_5$O$_7$PS: C,54.63:H,3.84:N,10.27:S,4.70. Found: C,54.01:H,4.08:N,10.00:S,4.99 and 5.13: Na, 0.33 and 0.37: KF(HOH), 0.69 and 0.80.

Crystallization

A sample of (2R,3R)-3-[4-(4-cyanophenyl)thiazol-2-yl]-2-(2,4-difluorophenyl)-1-(1H-1,2,4-triazol-1-yl)-2-[[(m-(di-t-butylphosphonooxy)benzoyloxy]methoxy]butane prepared as in Example 3 was dissolved in methylene chloride (75 ml). Trifluoroacetic acid (TFA) (25 ml) was added and the solution was stirred for 15 minutes. The solution was concentrated and diluted with CCl$_4$. The mixture was reconcentrated and diluted with 100 ml of ice cold water. The resulting mixture was extracted with ethyl acetate (150 ml). The ethyl acetate layer was washed (water, brine), dried (sodium sulfate) and concentrated to leave the free acid as an oil which turned granular when stirred with ether.

A sample of this crude acid (600 mg) was purified using a Shimadzu Prep HPLC (YMC ODS 30×100 mm column and eluting with a gradient starting with 40% B-60% A and proceeding to 100% B over 10 minutes). The solvents were removed by lyophilization to leave the title compound as a white solid (400 mg). The solid was dissolved in acetonitrile (175 mL) at 80° C. The clear solution was kept at 80° C. and then slowly cooled and allowed to stand at ambient temperatures for 18 hours to afford the crystalline title material (280 mg, 70% recovery).

A single crystal X-ray was obtained which confirmed the structure.

1. Purity about 90%.
2. Solvent A=10% methanol–90% water–0.1% TFA. Solvent B=90% methanol–10% water–0.1% TFA.

Example 4

(2R,3R)-3-[4-(cyanophenyl)thiazol-2-yl]-2-(2,4-difluorophenyl)-1-(1H-1,2,4-triazol-1yl)-2-[[[[p-phosphonooxymethyl]benzoyloxy]methoxy]carbonyloxy]butane

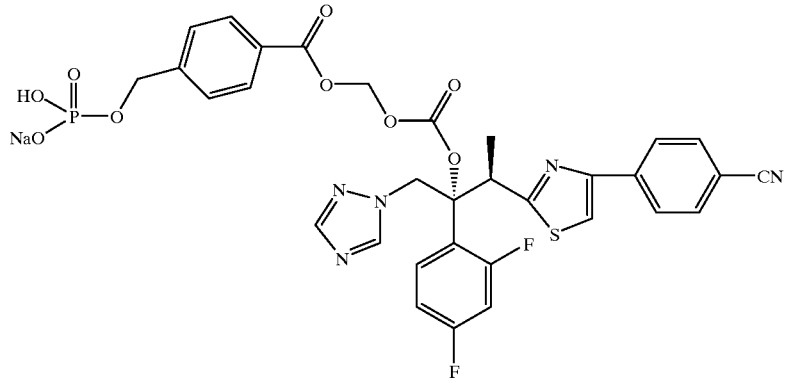

(2R,3R)-3-[4-(4-cyanophenyl)thiazol-2-yl]-2-(2,4-difluorophenyl)-1-(1H-1,2,4-triazol-1-yl)-2-[[chloromethoxy]carbonyloxy]butane

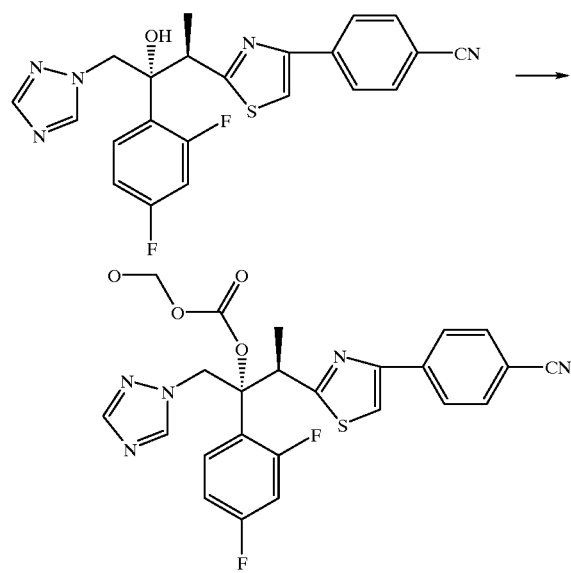

(2R,3R)-3-[4-(4-cyanophenyl)thiazol-2-yl]-2-(2,4-difluorophenyl)-1-(1H-1,2,4-triazol-1-yl)butan-2-ol (5.8 mmol) was added to a suspension of potassium hydride (7 mmol) in THF at 0C and was allowed to stir for 0.5 hours. Chloromethyl chloroformate (5.8 mmol, in 2mL THF) was added dropwise and the reaction was allowed to warm to room temperature and stirred for 4 hours. The crude reaction was diluted with EtOAc, and was sequentially washed with H$_2$O, 0.1N HCl, H$_2$O, and brine. The organic layer was dried over MgSO$_4$ and was concentrated to afford 3.43 g of the subtitled product as a pale yellow solid. $^1$H NMR (DMSO) δ 8.47 (s, 1H), 8.29 (s, 1H), 8.08 (s, 1H), 7.97 (d, 2H, J=8), 7.88 (d, 2H, J=8), 7.26–7.12 (m, 3H), 5.93 (d, 1H, J=6), 5.90 (d, 1H, J=6), 5.70 (d, J=1H, J=15), 5.36 (d, 1H, J=15), 4.02 (q, 1H, J=7), and 1.48 (d, 3H, J=7); MS (MH+=530).

(2R,3R)-3-[4-(4-cyanophenyl)thiazol-2-yl]-2-(2,4-difluorophenyl)-1-(1H-1,2,4-triazol-1yl)-2-[[1p-hydroxymethyl]benzoyloxy]methoxy]carbonyloxy]butane

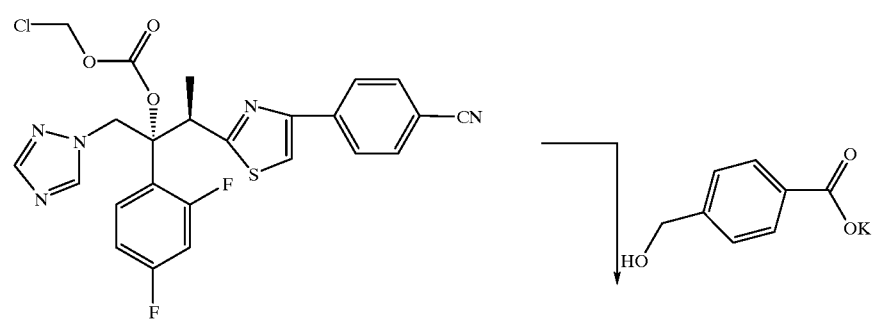

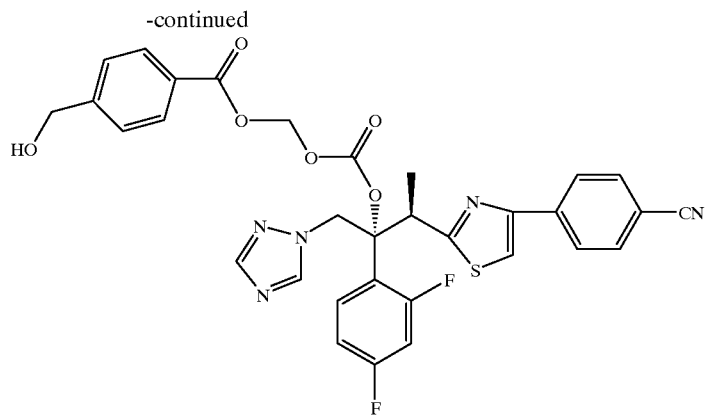

(2R,3R)-3-[4-(4-cyanophenyl)thiazol-2-yl]-2-(2,4-difluorophenyl)1-(1H-1,2,4-triazol-1yl)-2-[[chloromethyl]methyloxy]butane (2R,3R)-3-[4-(4-cyanophenyl)thiazol-2-yl]-2-(2,4-difluorophenyl)1-(1H-1,2,4-triazol-1yl)-2-[[chloromethyl]methyloxy]butane (23.6 mmol) was added to an acetonitrile solution of hydroxymethyl benzoate potassium salt (28.3 mmol, prepared by the method of Lombardino et al, U.S. Pat. No. 4,623,486) and 18-crown-6 (23.6 mmol), and the reaction was allowed to warm to 60° C. and stir overnight under $N_2$. After cooling at rt, the mixture was filtered and the solution was concentrated at reduced pressure. The residue was purified via column chromatography on silica yielding 9.5 g (62%) of the subtitled compound as a white solid. $^1$H NMR (DMSO-$d_6$) δ 8.45 (s, 1H), 8.24 (s, 1H), 7.94 (dd, 4H, J=8, 2), 7.85 (s, 1H), 7.84 (d, 2H, J=8), 7.49 (d, 2H, J=8), 7.21–7.03 (m, 3H), 5.95 (s, 2H), 5.67 (d, 1H, J=15), 5.42 (br s, 1H), 5.35 (d, 1H, J=15), 4.60 (s, 2H), 4.01 (q, 1H, J=7), 1.45 (d, 3H, J=7).

(2R,3R)-3-[4-(4-cyanophenyl)thiazol-2-yl]-2-(2,4-difluorophenyl)-1-(1H-1,2,4-triazol-1yl)-2-[[[p-di-t-butylphosphonooxymethyl]benzoyloxy]methoxy]carbonyloxy]butane

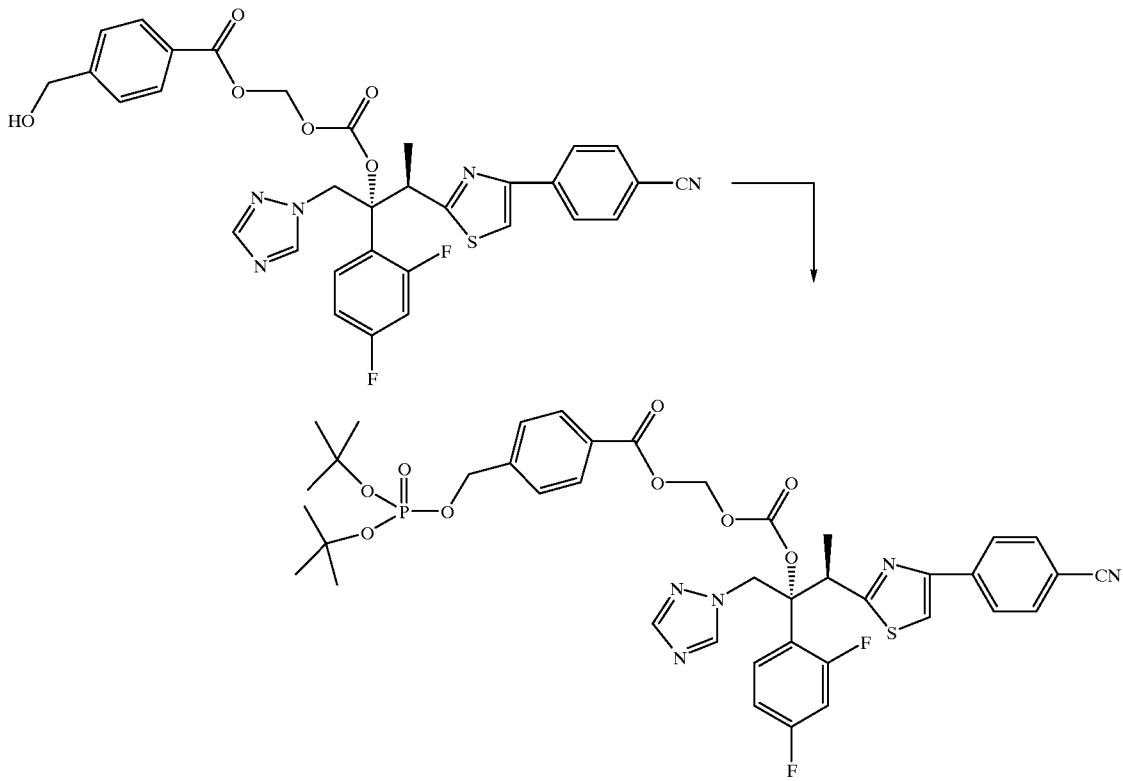

A mixture of (2R,3R)-3-[4-(4-cyanophenyl)thiazol-2-yl]-2-(2,4-difluorophenyl)-1-(1H-1,2,4-triazol-1yl)-2-[[[p-hydroxymethyl]benzoyloxy]methoxy]carbonyloxy]butane (14.7 mmol), di-tert-butylphosphorous amidite (29.4 mmol) and tetrazole (73.5 mmol) in 150 mL of THF was stirred at rt overnight. It was then cooled to −78° C. and MCPBA (32.3 mmol) in $CH_2CL_2$ was added via a syringe under $N_2$. After addition, it was warmed to rt and stirred for another hour. Aqueous $NaHSO_3$ was then added and the mixture was stirred at rt for 15 min. The crude reaction was diluted with EtOAc, and was sequentially washed with NaHSO$_3$, NaHCO$_3$ and water. The organic layer was dried over Na$_2$SO4 and then was concentrated. The residue was purified via column chromatography on silica (Hexane/EtoAc) to afford 8.8 g (71%) of the subtitled compound as a white solid. $^1$H NMR (DMSO-d$_6$) δ 8.25 (s, 1H), 8.22 (s, 1H), 7.96 (d, 2H, J=8), 7.93 (d, 2H, J=8), 7.84 (s 1H), 7.82 (d, 2H, J=8), 7.54 (d, 2H, J=8), 7.30–7.01 (m, 3H), 5.96 (s, 2H), 5.67 (d, 1H, J=15), 5.35 (d, 1H, J=15), 5.04 (d, 2H, J=8), 4.01 (q, 1H, J=7), 1.45 (d, 3H, J=7), 1.42 (s, 9H).

(2R,3R)-3-[4-(4-cyanophenyl)thiazol-2-yl]-2-(2,4-difluorophenyl)-1-(1H-1,2,4-triazol-1yl)-2-[[[[p-phosphonooxymethyl]benzoyloxy]methoxy]carbonyloxy]butane Trifluoroacetic acid (210 mmol) was added to a mixture of (2R,3R)-3-[4-(4-cyanophenyl)thiazol-2-yl]-2-(2,4difluorophenyl)-1-(1H-1,2,4-triazol-1yl)-2-[[[[-p-(di-t-butylphosphonooxymethyl]benzoyloxy]methoxy]carbonyloxy]butane (10.5 mmol) in 300 mL of CH$_2$CL$_2$ at 0° C. under N$_2$. The reaction mixture was then allowed to warm to rt and stirred for 1 h. After evaporation of volatiles in vacuo, the residue was dissolved in a minimum amount of CH$_3$CN and basified with saturated aqueous NaHCO$_3$ until pH was 8.5. It was then purified via C-18 column chromatography (H$_2$O to 20% H$_2$O/CH$_3$CN to CH$_3$CN). After lyopholization, 2.0 g (25%) of the product was obtained as a white solid. $^1$H NMR (DMSO-d$_6$) δ 8.45 (s, 1H), 8.23 (s, 1H), 7.98 (d, 2H, J=8), 7.93 (d, 2H, J=8), 7.85 (s, 1H), 7.84 (d, 2H, J=8), 7.55 (d, 2H, J=8), 7.18–7.04 (m, 3H), 5.95 (s, 2H), 5.67 (d, 1H, J=15), 5.34 (d, 1H, J=15), 4.99 (d, 2H, J=7), 4.01 (q, 1H, J=7), 3.37 (br s, 2H), 1.45 (d, 3H, J=7).

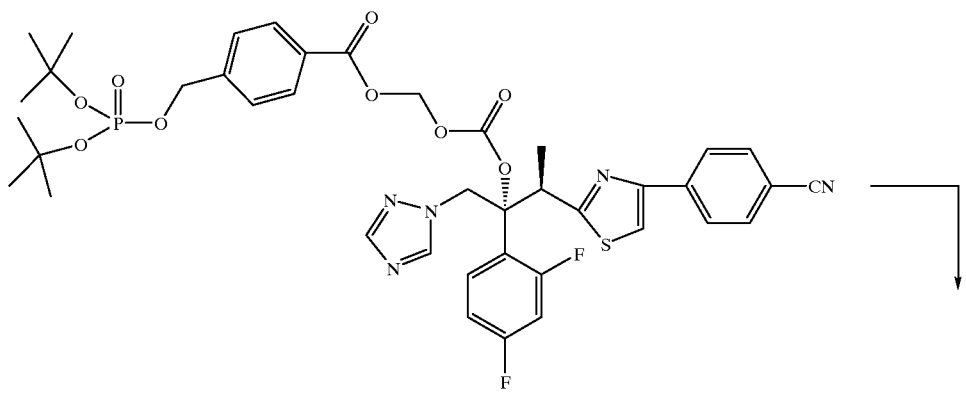

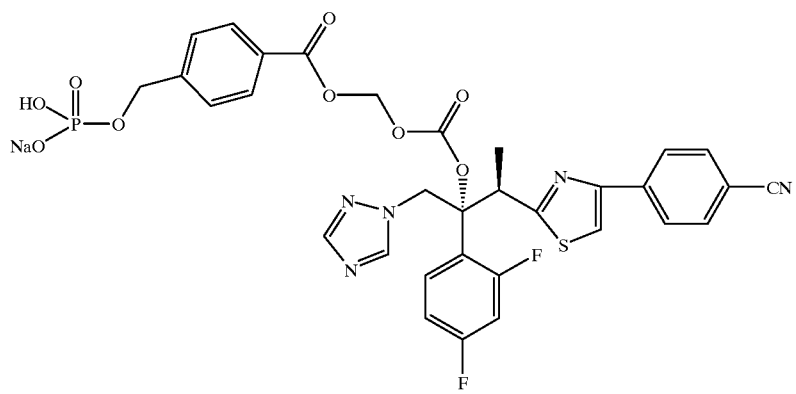

Example 5

(2R,3R)-3-[4-(4-cyanophenyl)thiazol-2-yl]-2-(2,4-difluorophenyl)-1-(1H-1,2,4-triazol-1yl)-2-[[[[m-phosphonooxy]benzoyloxy]methoxy]butane (2R,3R)-3-[4-(4-cyanophenyl)thiazol-2-yl]-2-(2,4-difluorophenyl)-1-(1H-1,2,4-triazol-1-yl)-2-[[(m-(benzyloxy)benzoyloxy]methoxy]butane

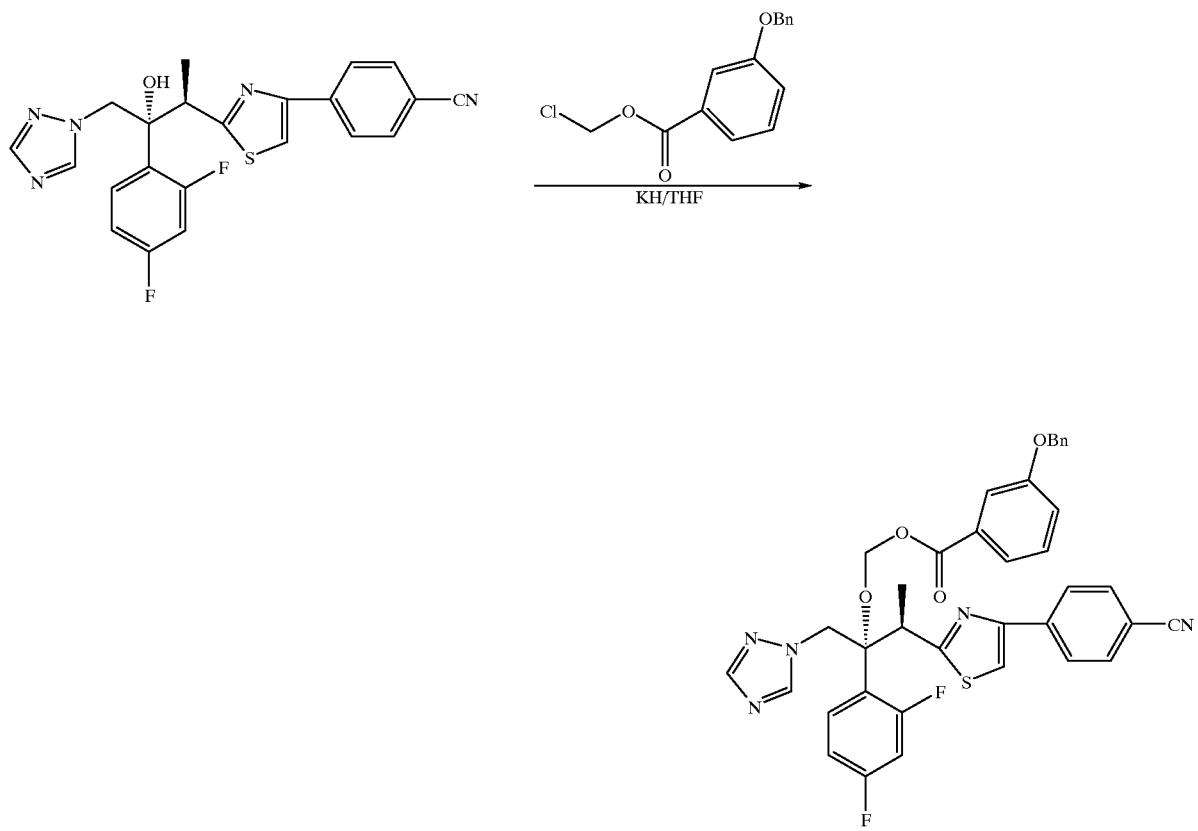

(2R,3R)-3-[4-(4-cyanophenyl)thiazol-2-yl]-2-(2,4-difluorophenyl)-1-(1H-1,2,4-triazol-1-yl)butan-2-ol (1.4 mmol) was added to a suspension of potassium hydride (1.5 mmol) in THF (10 mL) at room temperature. The mixture was stirred for 10 minutes and chloromethyl ether (1.6 mmol) was added. The reaction was allowed to stir at 32° C. for 5 hours. Excess base was carefully quenched with water, and the crude mixture was extracted into ethyl acetate. The organic layer was washed with water, brine and dried over $Na_2SO_4$. Purification of the crude product via flash chromatography (Hexanes/EtOAc 3/1) yielded 350 mg of the subtitled compound as a white solid. $^1$H NMR (300 MHz, $CDCl_3$) δ=1.29 (d, 3H), 4.12 (q, 1H), 4.99–5.03 (m, 3H), 5.32 (d, 1H), 6.19 (m, 2H), 6.76–6.88 (m, 2H), 7.08–7.38 (m, 3H), 7.32–7.48 (m, 8H), 7.88 (d, 2H), 8.14 (s, 1H). MS(ESI) 677.

(2R,3R)-3-[4-(4-cyanophenyl)thiazol-2-yl]-2-(2,4-difluorophenyl)-1-(1H-1,2,4-triazol-1-yl)-2-[[(m-hydroxy)benzoyloxy]methoxy]butane

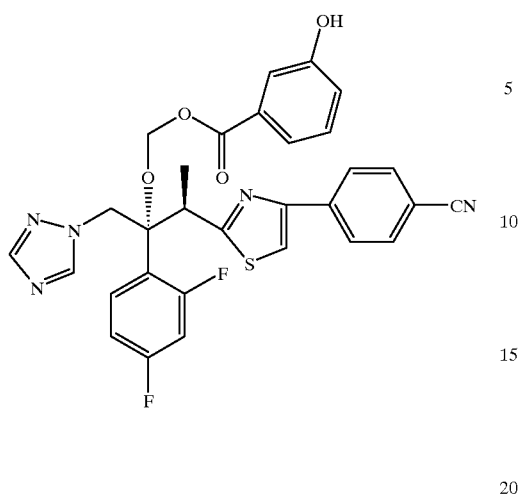

A suspension of (2R,3R)-3-[4-(4-cyanophenyl)thiazol-2-yl]-2-(2,4-difluorophenyl)-1-(1H-1,2,4-triazol-1-yl)-2-[[(m-(benzyloxy)benzoyloxy]methoxy]butane (0.40 mmol) in ethanol (150 mL) was hydrogenated over 10% Palladium on carbon (150 mg) at room temperature at 1 atmosphere for 12 hours. The mixture was then filtered and the filtrate concentrated. Purification of the crude product via flash chromatography (Hexanes/EtOAc 3/1) yielded 170 mg of the subtitled compound as a white solid. $^1$H NMR (300 MHz, CDCl$_3$) δ=1.29 (d, 3H), 4.10 (m, 1H), 5.09 (d, 2H), 5.33 (d, 2H), 5.94 (d, 2H), 6.14 (dd, 2H), 6.85 (m, 2H), 7.01 (d, 1H), 7.18–7.27 (m, 2H), 7.32–7.44 (m, 2H), 7.50 (s, 1H), 7.69 (d, 2H), 7.77 (m, 1H), 7.95 (d, 2H), 8.42 (s, 1H). MS(ESI) 587.

(2R,3R)-3-[4-(4-cyanophenyl)thiazol-2-yl]-2-(2,4-difluorophenyl)-1-(1H-1,2,4-triazol-1-yl)-2-[[(m-di-t-butylphosphonooxy)benzoyloxy]methoxy]butane

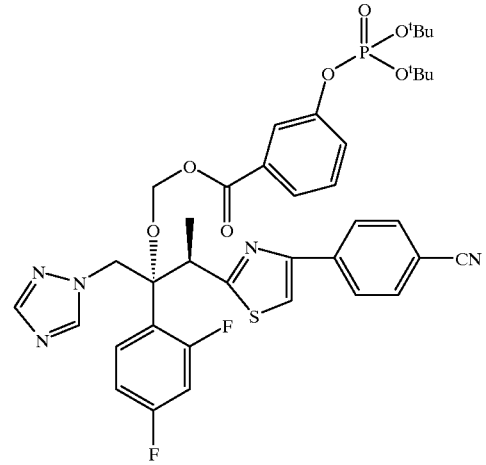

(2R,3R)-3-[4-(4-cyanophenyl)thiazol-2-yl]-2-(2,4-difluorophenyl)-1-(1H-1,2,4-triazol-1-yl)-2-[[(m-(hydroxy)benzyloxy]methoxy]butane (220 mg, 0.37 mmol), 1H-tetrazole (78 mg, 1.12 mmol), 4-dimethylaminopyridine (18 mg, 0.15 mmol) and di-t-butyl diisopropylphosphoramidite (0.24 mL, 0.75 mmol) in methylene chloride were refluxed under a nitrogen atmosphere for 12 hours. The mixture was then cooled to 0° C., and hydrogen peroxide (0.38 mL, 30% solution in water) was added dropwise at a rate which maintained the reaction temperature below 10° C. The resulting mixture was stirred at 20° C for 30 minutes before separating the organic layer, which was washed with water, dried over Na$_2$SO$_4$. Purification of the crude product via flash chromatography (Hexanes/EtOAc) yielded 200 mg of the subtitled compound as a white solid. $^1$H NMR (300 MHz, CDCl$_3$) δ=1.29 (d, 3H), 1.53 (s, 9H), 1.54 (s, 9H), 4.13 (q, 1H), 4.98 (d, 1H), 5.34 (dd, 1H), 6.20 (dd, 2H), 6.77–6.92 (m, 2H), 7.19–7.24 (m, 1H), 7.36–7.45 (m, 2H), 7.55–7.58 (m, 2H), 7.67 (s, 1H), 7.69 (d, 2H), 7.79 (m, 1H), 7.95 (dd, 2H), 8.12 (s, 1H). MS(ESI) 779.

(2R,3R)-3-[4-(4-cyanophenyl)thiazol-2-yl]-2-(2,4-difluorophenyl)-1-(1H-1,2,4-triazol-1-yl)-2-[[(m-phosphonooxy)benzoyloxy]methoxy]butane

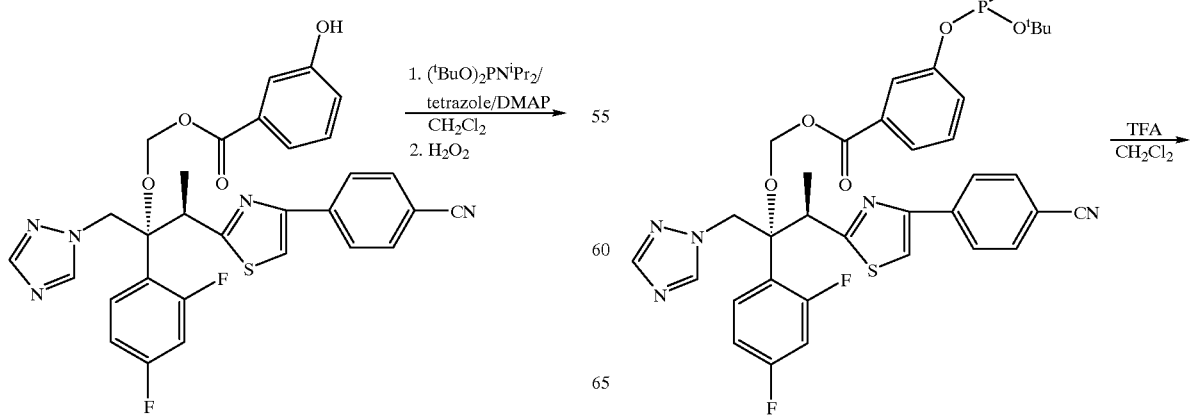

-continued

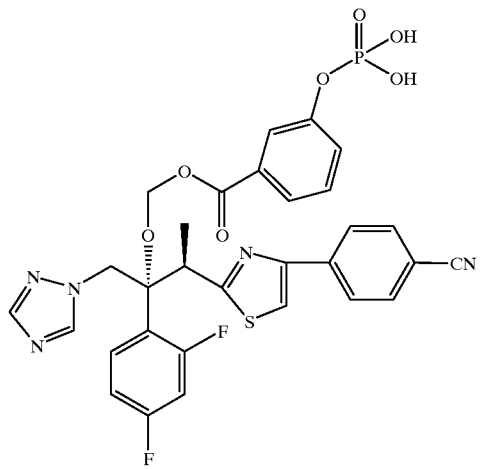

(2R,3R)-3-[4-(4-cyanophenyl)thiazol-2-yl]-2-(2,4-difluorophenyl)-1-(1H-1,2,4-triazol-1-yl)-2-[[(m-(di-t-butylphosphonooxy)benzoyloxy]methoxy]butane (180 mg) was dissolved in methylene chloride (20 mL). TFA (5 mL) was added and the solution stirred for 15 minutes. The solution was concentrated to leave a gum. Purification of the crude product via Prep-HPLC (MeOH/H$_2$O) yielded 120 mg of the titled compound as a white solid. $^1$H NMR (300 MHz, CDCl$_3$) δ=1.39 (d, 3H), 4.13 (q, 1H), 5.32 (dd, 2H), 5.66 (d, 1H), 5.93 (d, 1H), 6.79–6.92 (m, 2H), 7.22–7.25 (m, 3H), 7.59 (s, 1H), 7.62–7.66 (m, 4H), 7.84 (s, 1H), 7.94 (d, 2H), 8.82 (s, 1H). MS(ESI) 667.

Example 6

(2R,3R)-3-[4-(4-cyanophenyl)thiazol-2-yl]-2-(2,4-difluorophenyl)-1-(1H-1,2,4-triazol-1yl)-2-[[m-phosphonooxy]benzoyloxy]methoxy]carbonyloxy]butane

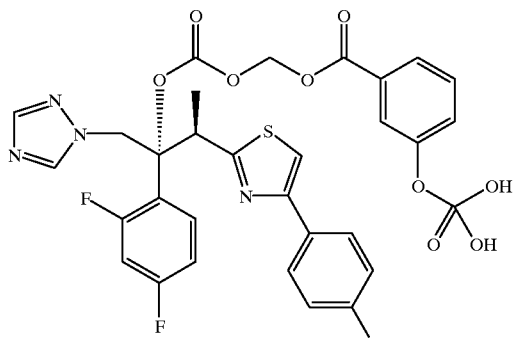

(2R,3R)-3-[4-(4-cyanophenyl)thiazol-2-yl]-2-(2,4-difluorophenyl)-1-(1H-1,2,4-triazol-1yl)-2-[[m-hydroxy]benzoyloxy]methoxy]carbonyloxy]butane

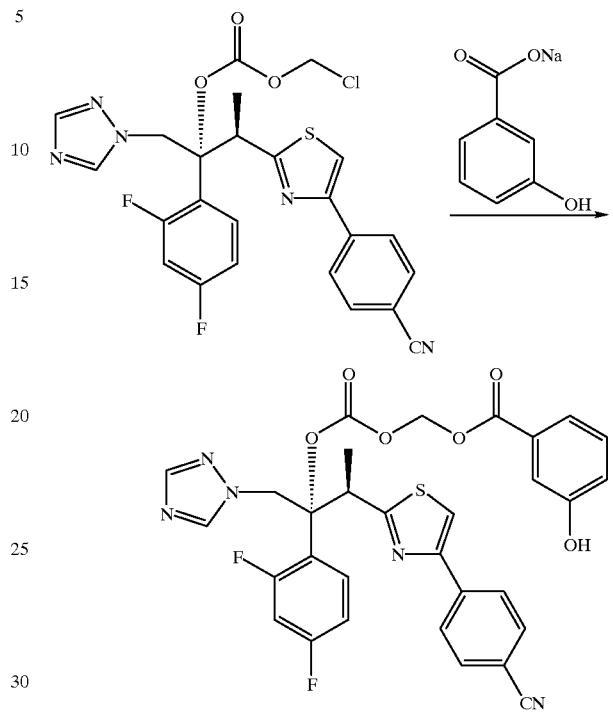

(2R,3R)-3-[4-(4-cyanophenyl)thiazol-2-yl]-2-(2,4-difluorophenyl)-1-(1H-1,2,4-triazol-1yl)-2-[[chloromethyl]methyloxy]carbonyloxy]butane (1.06 g, 2.0 mmol), 3-hydroxybenzoic acid sodium salt (0.32 g, 2.0 mmol) and 18-crown-6 (0.10 g) were stirred under nitrogen in CH$_3$CN (20 mL) and DMF (10 mL) at 65° C. for 20 hours. After cooling to room temperature the mixture was concentrated at reduced pressure. The residue was dissolved in CH$_3$CN and was purified by preparative HPLC to yield 1.0 g crude subtitled compound as an off white solid (79%). $^1$H NMR (DMSO-d$_6$) δ 9.93 (s, 1H), 8.48 (s, 1H), 8.25 (m, 4H), 7.95 (d, 2H, J=8), 7.83 (m, 2H), 7.49–7.08 (m, 5H), 5.95 (s, 2H), 5.68 (d, 1H, J=15), 5.37 (d, 1H, J=15), 4.00 (q, 1H, J=7), 1.45 (d, 3H, J=7). LC/MS (ESI+(MH+) 632 obs).

In a similar manner, p-hydroxy and o-hydroxy derivatives were also prepared.

(2R,3R)-3-[4-(4-cyanophenyl)thiazol-2-yl]-2-(2,4-difluorophenyl)-1-(1H-1,2,4-triazol-1yl)-2-[[p-hydroxy]benzoyloxy]methoxy]carbonyloxy]butane $^1$H NMR (DMSO-d$_6$) δ 10.51 (s, 1H), 8.44 (s, 1H), 8.23 (s, 1H), 7.92 (d, 2H, J=9), 7.83 (m, 4H), 7.22–7.02 (m, 3H), 6.86 (d, 2H, J=9), 5.89 (s, 2H), 5.66 (d, 1H, J=15), 5.34 (d, 1H, J=15), 3.99 (q,1H, J=7), 1.44 (d, 3H, J=7). MS (ESI+ (MH+) 632 obs).

(2R,3R)-3-[4-(4-cyanophenyl)thiazol-2-yl]-2-(2,4-difluorophenyl)-1(1H-1,2,4-triazol-1yl)-2-[[o-hydroxy]benzoyloxy]methoxy]carbonyloxy]butane $^1$H NMR (DMSO-d$_6$) δ 10.22 (s, 1H), 8.47 (s, 1H), 8.25 (s, 1H), 7.94 (d, 2H, J=9), 7.87 (s, 1H), 7.84 (d, 2H, J=9), 7.74 (dd, 1H, J=2,8), 7.55 (ddd, 1H, J=7,7,2), 7.22–7.03 (m, 3H), 7.01 (dd, 1H, J=7,2), 6.95 (ddd, 1H, J=7,7,2), 5.96 (s, 2H), 5.68 (d, 1H, J=15), 5.35 (d, 1H, J=15), 4.00 (q, 1H, J=7), 1.46 (d, 3H, J=7). MS (ESI+(MH+) 632 obs).

(2R,3R)-3-[4-(4-cyanophenyl)thiazol-2-yl]-2-(2,4-difluorophenyl)-1-(1H-1,2,4-triazol-1-yl)-2-[[m-phosphonooxy]benzoyloxy]methoxy]carbonyloxy]butane

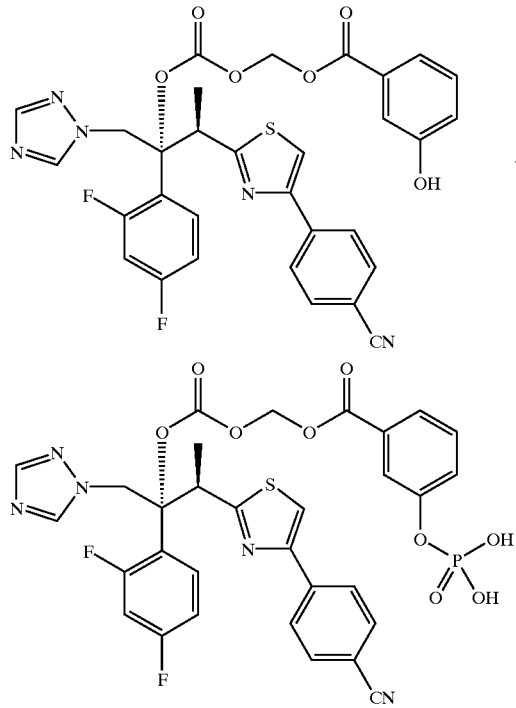

The crude (2R,3R)-3-[4-(4-cyanophenyl)thiazol-2-yl]-2-(2,4-difluorophenyl)-1-(1H-1,2,4-triazol-1-yl)-2-[[m-hydroxy]benzoyloxy]methyloxy]carbonyloxy]butane (792 mg, 1.26 mmol) was dissolved in $CH_2Cl_2$ (15 mL) and was cooled to 0° C. To this solution was added pyridine (0.38 mL, 4.74 mmol) followed by phosphorus oxychloride (0.16 mL, 1.79 mmol). Mixture was stirred 0.5 hours at 0° C. then 2 hours at room temperature. Water (15 mL) was added to the mixture and stirred for 0.25 hours. The mixture was then concentrated under reduced pressure. The residue was dissolved in $CH_3CN$ (16 mL) and was purified by preparative HPLC resulting in 0.128 g (14%) of the subtitled compound as a white solid. $^1H$ NMR (DMSO-$d_6$) δ 8.47 (s, 1H), 8.22 (s, 1H), 8.05 (d, 1H, J=9), 7.96–7.75 (m, 6H), 7.59 (t, 1H, J=7), 7.48 (d, 1H, J=7), 7.21–7.03 (m, 3H), 5.96 (s, 2H), 5.68 (d, 1H, J=15), 5.35 (d, 1H, J=15), 4.00 (q, 1H, J=7), 1.46 (d, 3H, J=7). MS (ESI+(MH+) 712 obs).

Similarly, p-phosphonooxy derivative was prepared.

(2R,3R)-3-[4-(4-cyanophenyl)thiazol-2-yl]-2-(2,4-difluorophenyl)-1-(1H-1,2,4-triazol-1yl)-2-[[p-phosphonooxy]benzoyloxy]methoxy]carbonyloxy]butane, disodium salt $^1H$ NMR (DMSO-$d_6$) δ 8.40 (s, 1H), 8.13 (s, 1H), 7.91 (d, 2H, J=8), 7.81 (d, 3H, J=8), 7.75 (d, 2H, J=9), 7.25 (d, 2H, J=9), 7.25–7.02 (m, 3H), 5.88 (s, 2H), 5.62 (d, 1H, J=15), 5.35 (d, 1H, J=15), 4.03 (q, 1H, J=7), 1.43 (d, 3H, J=7). MS (ESI+(MH+) 712 obs).

The o-phosphonooxy analog was prepared by phosphoamidite reaction followed by oxidation.

(2R,3R)-3-[4-(4-cyanophenyl)thiazol-2-yl]-2-(2,4-difluorophenlyl)-1-1H-1,2,4-triazol-1yl)-2-[[o-phosphonooxy]benzoyloxy]methoxy]carbonyloxy]butane (2R,3R)-3-[4-(4-cyanophenyl)thiazol-2-yl]-2-(2,4-difluorophenyl)-1(1H-1,2,4-triazol-1yl)-2-[[o-hydroxy]benzoyloxy]methoxy]carbonyloxy]butane (1.04g, 1.65 mmol), di t-butoxy diisopropyl phosphoramidite (0.91 g, 3.29 mmol), tetrazole (0.35g, 4.95 mmol) and 4-dimethyamino pyridine (0.08 g, 0.66 mmol was refluxed in THF (25 mL) for 18 hours. The reaction mixture was then cooled to 0° C. and to it was added 30% aqueous $H_2O_2$ (2.0 mL, 17.7 mmol). The reaction mixture was stirred 1 hour at 0° C. then 0.5 hours at room temperature and was then concentrated under reduced pressure. The residue was dissolved in $CH_2Cl_2$ and was washed with water and brine. The organic layer was dried over $Na_2SO_4$ and then was concentrated. The residue was then stirred in $CH_2Cl_2$ (50 mL) and TFA (25 mL) for 3 hours at room temperature. The reaction mixture was concentrated under reduced pressure and the residue was subjected to reverse phase chromatography on C-18 ($CH_3CN/H_2O$). The product containing fractions were concentrated under reduced pressure, frozen and lyophilized to afford 0.22g (19%) of the subtitled compound as a white solid. $^1H$ NMR (DMSO-$d_6$) δ 8.50 (s, 1H), 8.28 (s, 1H), 7.97 (s, 1H), 7.94 (d, 2H, J=9), 7.85 (d, 2H, J=9), 7.75 (d, 1H, J=7), 7.63 (dd, 1H, J=7,7), 7.42 (d, 1H, J=7), 7.26 (dd, 1H, J=7), 7.21–7.02 (m, 3H), 5.90 (s, 2H), 5.70 (d, 1H, J=15), 5.37 (d, 1H, J=15), 4.00 (q, 1H, J=7), 1.46 (d, 3H, J=7). MS (ESI+(MH+) 712 obs).

We claim:

1. A compound of the formula

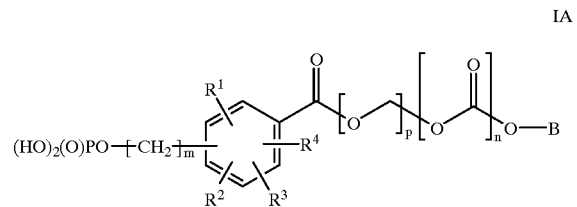

IA wherein B is either

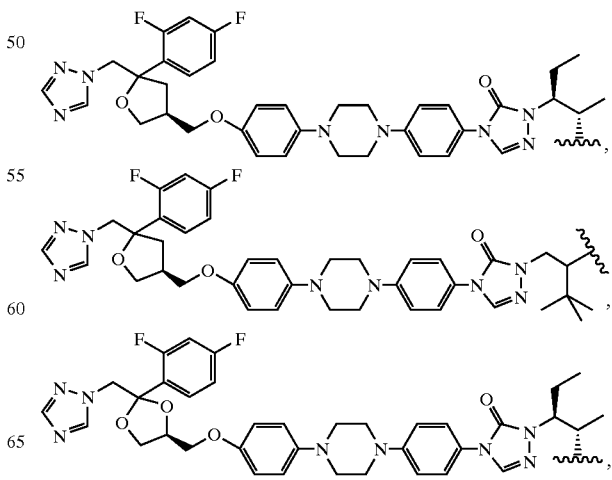

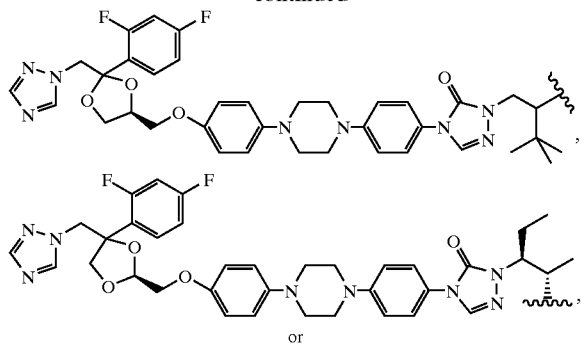
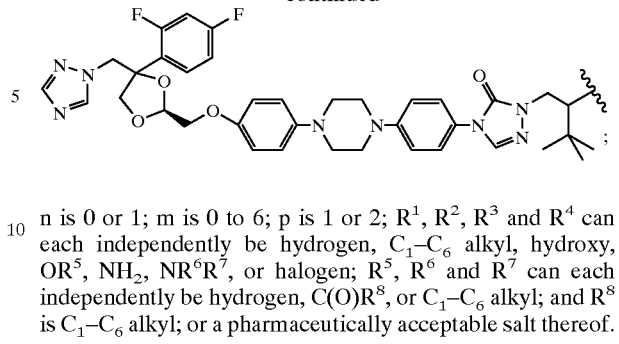
n is 0 or 1; m is 0 to 6; p is 1 or 2; $R^1$, $R^2$, $R^3$ and $R^4$ can each independently be hydrogen, $C_1$–$C_6$ alkyl, hydroxy, $OR^5$, $NH_2$, $NR^6R^7$, or halogen; $R^5$, $R^6$ and $R^7$ can each independently be hydrogen, $C(O)R^8$, or $C_1$–$C_6$ alkyl; and $R^8$ is $C_1$–$C_6$ alkyl; or a pharmaceutically acceptable salt thereof.
* * * * *